(12) United States Patent
Ben-Asher et al.

(10) Patent No.: US 11,045,453 B1
(45) Date of Patent: Jun. 29, 2021

(54) SERINE PROTEASE INHIBITOR FOR TREATING CORONAVIRUS INFECTION

(71) Applicant: RedHill Biopharma Ltd., Tel-Aviv (IL)

(72) Inventors: Dror Ben-Asher, Tel-Aviv (IL); Reza Fathi, Oradell, NJ (US)

(73) Assignee: RedHill Biopharma Ltd., Tel-Aviv (IL)

( * ) Notice: Subject to any disclaimer, the term of this patent is extended or adjusted under 35 U.S.C. 154(b) by 0 days.

(21) Appl. No.: 17/195,333

(22) Filed: Mar. 8, 2021

Related U.S. Application Data

(60) Provisional application No. 62/987,429, filed on Mar. 10, 2020, provisional application No. 63/003,601, filed on Apr. 1, 2020, provisional application No. 63/034,817, filed on Jun. 4, 2020, provisional application No. 63/074,799, filed on Sep. 4, 2020, provisional application No. 63/125,427, filed on Dec. 15, 2020.

(51) Int. Cl.
| | | |
|---|---|---|
| A61K 31/435 | (2006.01) | |
| A61K 9/48 | (2006.01) | |
| A61P 31/14 | (2006.01) | |
| A61K 9/00 | (2006.01) | |

(52) U.S. Cl.
CPC .......... *A61K 31/435* (2013.01); *A61K 9/0053* (2013.01); *A61K 9/48* (2013.01); *A61P 31/14* (2018.01)

(58) Field of Classification Search
CPC .................................................. A61K 31/435
See application file for complete search history.

(56) References Cited

U.S. PATENT DOCUMENTS

| | | |
|---|---|---|
| 6,624,169 B1 | 9/2003 | Wilhelm et al. |
| 6,861,435 B2 | 3/2005 | Ziegler |
| 7,211,670 B2 | 5/2007 | Ziegler et al. |
| 7,247,724 B2 | 7/2007 | Wosikowski-Buters et al. |
| 7,338,961 B2 | 3/2008 | Smith et al. |
| 7,342,018 B2 | 3/2008 | Wilhelm et al. |
| 7,608,623 B2 | 10/2009 | Sperl et al. |
| 7,659,396 B2 | 2/2010 | Wosikowski-Buters et al. |
| 7,713,980 B2 | 5/2010 | Grunenberg et al. |
| 7,745,441 B1 | 6/2010 | Wikstrom et al. |
| 7,807,681 B2 | 10/2010 | Sperl et al. |
| 7,884,206 B2 | 2/2011 | Ziegler et al. |
| 7,951,943 B2 | 5/2011 | Greiving |
| 8,063,248 B2 | 11/2011 | Smith et al. |
| 8,324,237 B2 | 12/2012 | Smith et al. |
| 8,492,385 B2 | 7/2013 | Grunenberg et al. |
| 8,557,800 B2 | 10/2013 | Smith et al. |
| 8,642,761 B2 | 2/2014 | Ziegler et al. |
| 9,089,532 B2 | 7/2015 | Schmalix et al. |
| RE46,424 E | 6/2017 | Ziegler et al. |
| 9,844,540 B2 * | 12/2017 | Fathi .................... A61K 31/435 |

OTHER PUBLICATIONS

Yamaya et al. Pulmonary Pharmacology & Therapeutics, 2015, 33: 66-74 (abstract).*
Hofmann et al., "Susceptibility to SARS coronavirus S protein-driven infection correlated with expression of angiotensin converting enzyme 2 and infection can be blocked by soluble receptor", Biochemical and Biophysical Research Communication 319 (2004) 1216-1221.
Hoffmann et al. "Nafamostat Mesylate Blocks Activation of SARS-CoV-2: New Treatment for Covid-19". Antimicrobial Agents and Chemotherapy, vol. 64, Issue 6 (2020) 1-3.
Hoffmann et al. "SARS-CoV-2 Cell Entry Depends on ACE2 and TMPRSS2 and is Blocked by a Clinically Proven Protease Inhibitor." Cell 181 (2020) 1-10.
Shen et al. "TMPRSS2: A potential target for treatment of influenza virus and coronavirus infection." Biochimie 142 (2017) 1-10.
Huggins "Structural analysis of experimental drugs binding to SARS-CoV-2 target TMPRSS2" Journal of Molecular Graphics and Modelling 100 (2020) 1-7.
Wang et al. "A Unique Protease Cleavage Site Predicted in the Spike Protein of the Novel Pneumonia Coronavirus (2019-nCoV) Potentially Related to Viral Transmissibality" Virologica Sinica (2020) 35:337-339.
Iwata-Yoshikawa et al. "TMPRSS2 Contributes to Virus Spread and Immunopathology in the Airways of Murine Models after Coronavirus Infection" Journal of Virology (2019) 93(6) 1-15.
Kuwase et al. "Simultaneous Treatment of Human Bronchial Epithelial Cells with Serine and Cysteine Protease Inhibitors Prevents Severe Acute Respiratory Syndrome Coronavirus Entry" Journal of Virology (2012) 86(12) 6537-6545.

\* cited by examiner

*Primary Examiner* — Rei Tsang Shiao
(74) *Attorney, Agent, or Firm* — Greenberg Traurig, LLP

(57) ABSTRACT

The disclosure is directed to WX-671, as (L)- or (D)-enantiomers, and as E- or (Z)-isomers or (E/Z)-mixtures, and as free bases or as salts thereof, in preparing medicines for treating coronavirus infection or preventing diseases caused by coronavirus infection, and a medicine for preventing coronavirus infection or preventing diseases caused by coronavirus infection.

30 Claims, 7 Drawing Sheets

SERINE PROTEASE INHIBITOR FOR TREATING CORONAVIRUS INFECTION

CROSS-REFERENCE TO RELATED APPLICATIONS

This application claims the benefit of U.S. Provisional Application No. 62/987,429, filed Mar. 10, 2020; U.S. Provisional Application No. 63/003,601, filed Apr. 1, 2020; U.S. Provisional Application No. 63/034,817 filed Jun. 4, 2020; U.S. Provisional Application No. 63/074,799, filed Sep. 4, 2020; and U.S. Provisional 63/125,427 filed Dec. 15, 2020. These applications are incorporated by reference in their entireties for all purposes.

BACKGROUND

Coronaviruses are lipid enveloped positive-stranded RNA viruses (+ss RNA) that replicate in the cell cytoplasm. Prior to 2002, coronaviruses were not considered to be significant human pathogens. Other human coronaviruses such as HCoV-229E and HCoV-OC43 resulted in only mild respiratory infections in healthy adults. In 2002, however, severe acute respiratory syndrome coronavirus (SARS-CoV) emerged in Guangdong Province, China. While SARS-CoV predominantly impacted Southeast Asia, with significant outbreaks throughout China, Hong Kong, Taiwan, Singapore, and Vietnam, the virus was carried outside the region.

In 2012, Middle East respiratory syndrome coronavirus (MERS-CoV), was detected in a patient with severe respiratory disease in Saudi Arabia. The clinical features of MERS-CoV infection in humans range from asymptomatic to very severe pneumonia with the potential development of acute respiratory distress syndrome, septic shock, and multiorgan failure resulting in death. Since the first case of MERS-CoV infection was reported and the virus was isolated, significant progress has been made toward understanding the epidemiology, ecology, and biology of the virus. Several assays for the detection of acute infection with MERS-CoV by real-time reverse transcription (RT)-PCR have been developed and are in widespread use.

In 2019, a novel coronavirus (nCoV) emerged in the world and is now known to cause coronavirus disease 2019 (COVID-19). COVID-19 is an infectious disease caused by severe acute respiratory syndrome coronavirus 2 (SARS coronavirus-2 or SARS-CoV-2), a virus phylogenetically closely related to SARS virus. The World Health Organization (WHO) has declared the 2019-2020 coronavirus outbreak to be a Public Health Emergency of International Concern (PHEIC). For most patients, COVID-19 begins and ends in their lungs, because coronaviruses primarily cause respiratory diseases.

SUMMARY

The present invention relates generally to the fields of virology, infectious disease and medicine. The invention provides a new use of WX-671 as (L)- or (D)-enantiomers, and as E- or (Z)-isomers or (E/Z)-mixtures, and as free bases or as salts thereof, in the preparation of medicines for treating coronavirus infection in humans.

According to aspects illustrated herein, there is disclosed a method for the treatment of the 2019 coronavirus disease (COVID-19) caused by the SARS-CoV-2 virus in a human in need thereof that includes administering an effective amount of WX-671, as (L)- or (D)-enantiomers, and as E- or (Z)-isomers or (E/Z)-mixtures, and as free bases or as salts thereof. In an embodiment, WX-671 exists as a hydrogen sulfate salt. In an embodiment, WX-671 is combined with a pharmaceutically-acceptable carrier material. In an embodiment, the WX-671 and optionally the pharmaceutically-acceptable carrier material, are in a unit dosage form suitable for oral administration. In an embodiment, the dosage form is a solid dosage form. In an embodiment, the solid dosage form is a capsule. In an embodiment, the SARS-CoV-2 virus is wild-type. In an embodiment, the SARS-CoV-2 virus is a naturally occurring coronavirus variant. In an embodiment, 200 mg of WX-671 is administered in a single capsule to a human in need thereof, once a day for at least 10 days, for a total daily dose of 200 mg. In an embodiment, 400 mg of WX-671 is administered in two capsules to a human in need thereof, once a day for at least 10 days, for a total daily dose of 400 mg. In an embodiment, about 231 mg of WX-671.1 (upamostat) is administered in a single capsule to a human in need thereof, once a day for at least 10 days, for a total daily dose equivalent to 200 mg of the free form. In an embodiment, about 463 mg of WX-671.1 (upamostat) is administered as two capsules to a human in need thereof, once a day for at least 10 days, for a total daily dose equivalent to 400 mg of the free form. In an embodiment, administration of the effective amount of WX-671 results in a decrease of viral load by at least 10%.

According to aspects illustrated herein, there is disclosed a method of treatment comprising administering an effective amount of WX-671, as (L)- or (D)-enantiomers, and as E- or (Z)-isomers or (E/Z)-mixtures, and as free bases or as salts thereof, to a human having 2019 coronavirus disease (COVID-19) caused by the SARS-CoV-2 virus. In an embodiment, WX-671 exists as a hydrogen sulfate salt. In an embodiment, WX-671 is combined with a pharmaceutically-acceptable carrier material. In an embodiment, WX-671 optionally with a pharmaceutically-acceptable carrier material, are in a unit dosage form suitable for oral administration. In an embodiment, the dosage form is a solid dosage form. In an embodiment, the solid dosage for is a capsule. In an embodiment, the SARS-CoV-2 virus is wild-type. In an embodiment, the SARS-CoV-2 virus is a naturally occurring coronavirus variant. In an embodiment, WX-671.1 (upamostat) is administered as a single capsule comprising 200 mg of the free base, and wherein a single capsule is administered to a human in need thereof once a day for at least 10 days, for a total daily dose of 200 mg. In an embodiment, WX-671.1 (upamostat) is administered as two capsules, each capsule comprising 200 mg, and wherein two capsules are administered to a human in need thereof once a day for at least 10 days, for a total daily dose of 400 mg.

According to aspects illustrated herein, there is disclosed WX-671, as (L)- or (D)-enantiomers, and as E- or (Z)-isomers or (E/Z)-mixtures, and as free bases or as salts thereof, for use in treating coronavirus infection.

According to aspects illustrated herein, there is disclosed WX-671, as (L)- or (D)-enantiomers, and as E- or (Z)-isomers or (E/Z)-mixtures, and as free bases or as salts thereof, for use in treating the 2019 coronavirus disease (COVID-19) caused by the SARS-CoV-2 virus.

According to aspects illustrated herein, there is disclosed (N-α-(2,4,6-triisopropylphenylsulfonyl)-3-hydroxyamidino-phenylalanine-4-ethoxycarbonylpiperazide) as (L)- or (D)-enantiomers, and as E- or (Z)-isomers or (E/Z)-mixtures, and as free bases or as salts thereof, for use in treating coronavirus infection.

According to aspects illustrated herein, there is disclosed (N-α-(2,4,6-triisopropylphenylsulfonyl)-3-hydroxyamidino-phenylalanine-4-ethoxycarbonylpiperazide) as (L)- or (D)-enantiomers, and as E- or (Z)-isomers or (E/Z)-mixtures, and as free bases or as salts thereof, for use in treating the 2019 coronavirus disease (COVID-19) caused by the SARS-CoV-2 virus.

According to aspects illustrated herein, there is disclosed use of WX-671, as (L)- or (D)-enantiomers, and as E- or (Z)-isomers or (E/Z)-mixtures, and as free bases or as salts thereof, for the manufacture of a medicament for treatment of coronavirus infection.

According to aspects illustrated herein, there is disclosed use of WX-671, as (L)- or (D)-enantiomers, and as E- or (Z)-isomers or (E/Z)-mixtures, and as free bases or as salts thereof, for the manufacture of a medicament for treatment of the 2019 coronavirus disease (COVID-19) caused by the SARS-CoV-2 virus.

According to aspects illustrated herein, there is disclosed use of (N-α-(2,4,6-triisopropylphenylsulfonyl)-3-hydroxy-amidino-phenylalanine-4-ethoxycarbonylpiperazide) as (L)- or (D)-enantiomers, and as E- or (Z)-isomers or (E/Z)-mixtures, and as free bases or as salts thereof, for the manufacture of a medicament for treatment of coronavirus infection.

According to aspects illustrated herein, there is disclosed use of (N-α-(2,4,6-triisopropylphenylsulfonyl)-3-hydroxy-amidino-phenylalanine-4-ethoxycarbonylpiperazide) as (L)- or (D)-enantiomers, and as E- or (Z)-isomers or (E/Z)-mixtures, and as free bases or as salts thereof, for the manufacture of a medicament for treatment of the 2019 coronavirus disease (COVID-19) caused by the SARS-CoV-2 virus.

According to aspects illustrated herein, there is disclosed a pharmaceutical composition for the treatment of coronavirus infection, comprising WX-671,

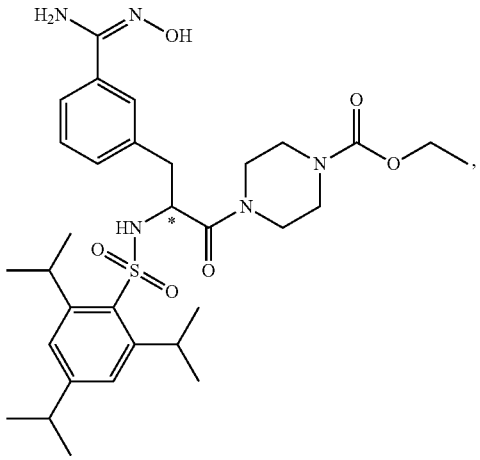 [SMILES: CCOC(=O)N1CCN(C(=O)C(Cc2cccc(/C(N)=N\O)c2)NS(=O)(=O)c2c(C(C)C)cc(C(C)C)cc2C(C)C)CC1]

as (L)- or (D)-enantiomers, and as E- or (Z)-isomers or (E/Z)-mixtures, and as free bases or as salts thereof.

According to aspects illustrated herein, there is disclosed a pharmaceutical composition for the treatment of the 2019 coronavirus disease (COVID-19) caused by the SARS-CoV-2 virus, comprising WX-671,

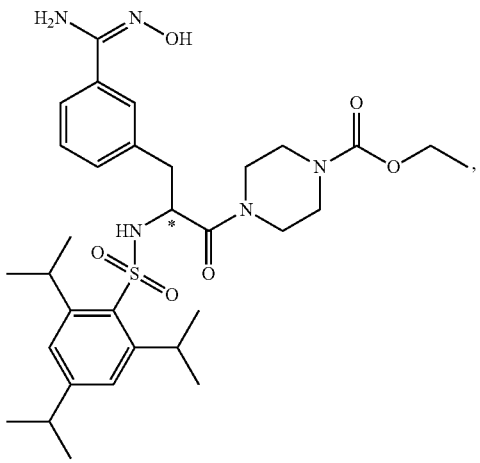 [SMILES: CCOC(=O)N1CCN(C(=O)C(Cc2cccc(/C(N)=N\O)c2)NS(=O)(=O)c2c(C(C)C)cc(C(C)C)cc2C(C)C)CC1]

as (L)- or (D)-enantiomers, and as E- or (Z)-isomers or (E/Z)-mixtures, and as free bases or as salts thereof.

According to aspects illustrated herein, there is disclosed a pharmaceutical composition for the treatment of coronavirus infection, comprising (N-α-(2,4,6-triisopropylphenylsulfonyl)-3-hydroxyamidino-phenylalanine-4-ethoxycarbonylpiperazide) as (L)- or (D)-enantiomers, and as E- or (Z)-isomers or (E/Z)-mixtures, and as free bases or as salts thereof.

According to aspects illustrated herein, there is disclosed a pharmaceutical composition for the treatment of the 2019 coronavirus disease (COVID-19) caused by the SARS-CoV-2 virus, (N-α-(2,4,6-triisopropylphenylsulfonyl)-3-hydroxyamidino-phenylalanine-4-ethoxycarbonylpiperazide) as (L)- or (D)-enantiomers, and as E- or (Z)-isomers or (E/Z)-mixtures, and as free bases or as salts thereof.

According to aspects illustrated herein, there is disclosed an anti-coronavirus infection agent comprising WX-671,

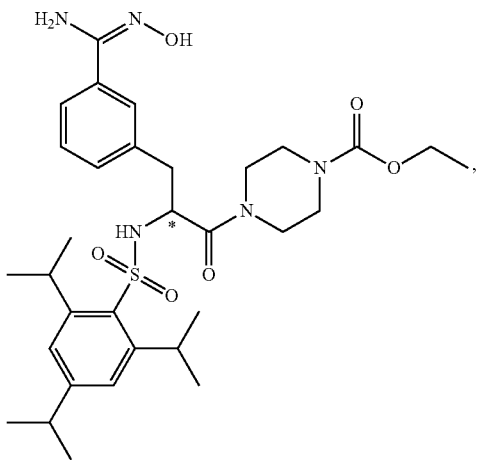 [SMILES: CCOC(=O)N1CCN(C(=O)C(Cc2cccc(/C(N)=N\O)c2)NS(=O)(=O)c2c(C(C)C)cc(C(C)C)cc2C(C)C)CC1]

as (L)- or (D)-enantiomers, and as E- or (Z)-isomers or (E/Z)-mixtures, and as free bases or as salts thereof.

According to aspects illustrated herein, there is disclosed an anti-coronavirus infection agent comprising (N-α-(2,4,6-triisopropylphenylsulfonyl)-3-hydroxyamidino-phenylalanine-4-ethoxycarbonylpiperazide) as (L)- or (D)-enantiomers, and as E- or (Z)-isomers or (E/Z)-mixtures, and as free bases or as salts thereof.

According to aspects illustrated herein, there is disclosed a method for the treatment of human coronavirus infection, comprising administering to a subject in need thereof a therapeutically effective amount of a compound selected from one of N-α(2,4,6-triisopropylphenylsulfonyl)-3-amidino-phenylalanine-4-ethoxy-carbonylpiperazide-hydrochloride or its prodrug N-α-(2,4,6-triisopropylphenylsulfonyl)-3-hydroxyamidino-phenylalanine-4-ethoxycarbonylpiperazide, wherein the selected compound can be present as (L)- or (D)-enantiomers, and as E- or (Z)-isomers or (E/Z)-mixtures, and as free bases or as salts thereof. In an embodiment, the method further comprises diagnostically confirming that the subject is infected with a human coronavirus prior to administering the compound. In an embodiment, the coronavirus infection is severe acute respiratory syndrome coronavirus 2 (SARS-CoV-2). In an embodiment, the compound is N-α-(2,4,6-triisopropylphenylsulfonyl)-3-hydroxyamidino-phenylalanine-4-ethoxycarbonylpiperazide and in an orally administrable form. In an embodiment, the compound is N-α(2,4,6-triisopropylphenylsulfonyl)-3-amidino-phenylalanine-4-ethoxy-carbonylpiperazide-hydrochloride and in an injectable form to be delivered intravenously or intramuscularly. In an embodiment, the compound is N-α-(2,4,6-triisopropylphenylsulfonyl)-3-hydroxyamidino-phenylalanine-4-ethoxycarbonylpiperazide present as a sulfate or hydrogen sulfate salt. In an embodiment, the compound is N-α-(2,4,6-triisopropylphenylsulfonyl)-3-hydroxyamidino-phenylalanine-4-ethoxycarbonylpiperazide present in the L-stereoisomer conformation. In an embodiment, the compound is N-α-(2,4,6-triisopropylphenylsulfonyl)-3-hydroxyamidino-(L)-phenylalanine-4-ethoxycarbonylpiperazinium hydrogen sulfate. In an embodiment, the compound is N-α-(2,4,6-triisopropylphenylsulfonyl)-3-hydroxyamidino-phenylalanine-4-ethoxycarbonylpiperazide and is to be administered in a dose of 200 mg per day. In an embodiment, the compound is N-α-(2,4,6-triisopropylphenylsulfonyl)-3-hydroxyamidino-phenylalanine-4-ethoxycarbonylpiperazide and is to be administered in a dose of 400 mg per day.

According to aspect illustrated herein, there is disclosed a method of treating COVID-19 (SARS-CoV-2) coronavirus infection, the method comprising administering to a subject in need thereof for at least 14 days one or more therapeutically effective doses of a compound selected from one of N-α(2,4,6-triisopropylphenylsulfonyl)-3-amidino-phenyl-alanine-4-ethoxy-carbonylpiperazide-hydrochloride or its prodrug N-α-(2,4,6-triisopropylphenylsulfonyl)-3-hydroxyamidino-phenylalanine-4-ethoxycarbonylpiperazide, wherein the selected compound can be present as (L)- or (D)-enantiomers, and as E- or (Z)-isomers or (E/Z)-mixtures, and as free bases or as salts thereof. In an embodiment, the method further comprises diagnostically confirming that the subject is infected with SARS-CoV-2 prior to administering the compound. In an embodiment, the total dose of the compound N-α-(2,4,6-triisopropylphenylsulfonyl)-3-hydroxyamidino-phenylalanine-4-ethoxycarbonylpiperazide per day is independently selected upon each occurrence from about 200 mg to about 400 mg. In an embodiment, the compound is N-α-(2,4,6-triisopropylphenylsulfonyl)-3-hydroxyamidino-(L)-phenylalanine-4-ethoxycarbonylpiperazinium hydrogen sulfate.

According to aspects illustrated herein, there is disclosed a method for treating COVID-19 (SARS-CoV-2) coronavirus infection, comprising administering to a human subject in need thereof a therapeutically acceptable amount of a compound selected from one of N-α(2,4,6-triisopropylphenylsulfonyl)-3-amidino-phenylalanine-4-ethoxy-carbonylpiperazide-hydrochloride or its prodrug N-α-(2,4,6-triisopropylphenylsulfonyl)-3-hydroxyamidino-phenylalanine-4-ethoxycarbonylpiperazide, wherein the selected compound can be present as (L)- or (D)-enantiomers, and as E- or (Z)-isomers or (E/Z)-mixtures, and as free bases or as salts thereof, the compound having the ability to bind a hemagglutinin (HA)-activating type II transmembrane serine proteases (TTSPs), thereby decreasing coronavirus replication in the human subject following exposure to coronavirus. In an embodiment, the TTSP is transmembrane protease serine SI member 2 (TMPRSS2). In an embodiment, the TTSP is transmembrane protease serine 11A (TMPRSS11(A)). In an embodiment, the method further comprises diagnostically confirming that the subject is infected with SARS-CoV-2 prior to administering the compound. In an embodiment, the compound is N-α-(2,4,6-triisopropylphenylsulfonyl)-3-hydroxyamidino-(L)-phenyl-alanine-4-ethoxycarbonylpiperazinium hydrogen sulfate.

According to aspects illustrated herein, there is disclosed a method of modulating replication of coronavirus in a host cell infected with the coronavirus comprising administering to the host cell a compound selected from one of N-α(2,4,6-triisopropylphenylsulfonyl)-3-amidino-phenylalanine-4-ethoxy-carbonylpiperazide-hydrochloride or its prodrug N-α-(2,4,6-triisopropylphenylsulfonyl)-3-hydroxyamidino-phenylalanine-4-ethoxycarbonylpiperazide, wherein the selected compound can be present as (L)- or (D)-enantiomers, and as E- or (Z)-isomers or (E/Z)-mixtures, and as free bases or as salts thereof, in an amount effective to modulate replication of the virus. In an embodiment, the compound is N-α-(2,4,6-triisopropylphenylsulfonyl)-3-hydroxyamidino-(L)-phenylalanine-4-ethoxycarbonylpiperazinium hydrogen sulfate.

According to aspects illustrated herein, there is disclosed use of WX-671 in the preparation of drugs for treating coronavirus infection. In an embodiment, the coronavirus is a 2019 novel coronavirus COVID-19. In an embodiment, the coronavirus infection is coronavirus pneumonia. In an embodiment, the WX-671 is active against a host serine protease inhibitor and blocks the spike protein-driven entry into host cells.

According to aspects illustrated herein, the present invention features a packaged pharmaceutical product. The packaged pharmaceutical product includes a container, a plurality of WX-671 unit dosage forms suitable for oral administration in the container, and a legend (e.g., a label or an insert) associated with the container and indicating administration of WX-671 for treating 2019 coronavirus disease (COVID-19) caused by the SARS-CoV-2 virus.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

FIG. 6A Calu-3 cells or FIG. 6B Vero-E6 cells were pre-incubated with the indicated concentrations of upamostat, WX-UK1, camostat mesylate, or chloroquine and subsequently inoculated with pseudoparticles harboring the VSV-SARS-2 S protein. Pseudotype entry was analyzed by determining luciferase activity in cell lysates. The results of a single experiment performed with quadruplicate samples are shown. Error bars indicate standard deviation (SD).

DEFINITIONS

Figure 1:
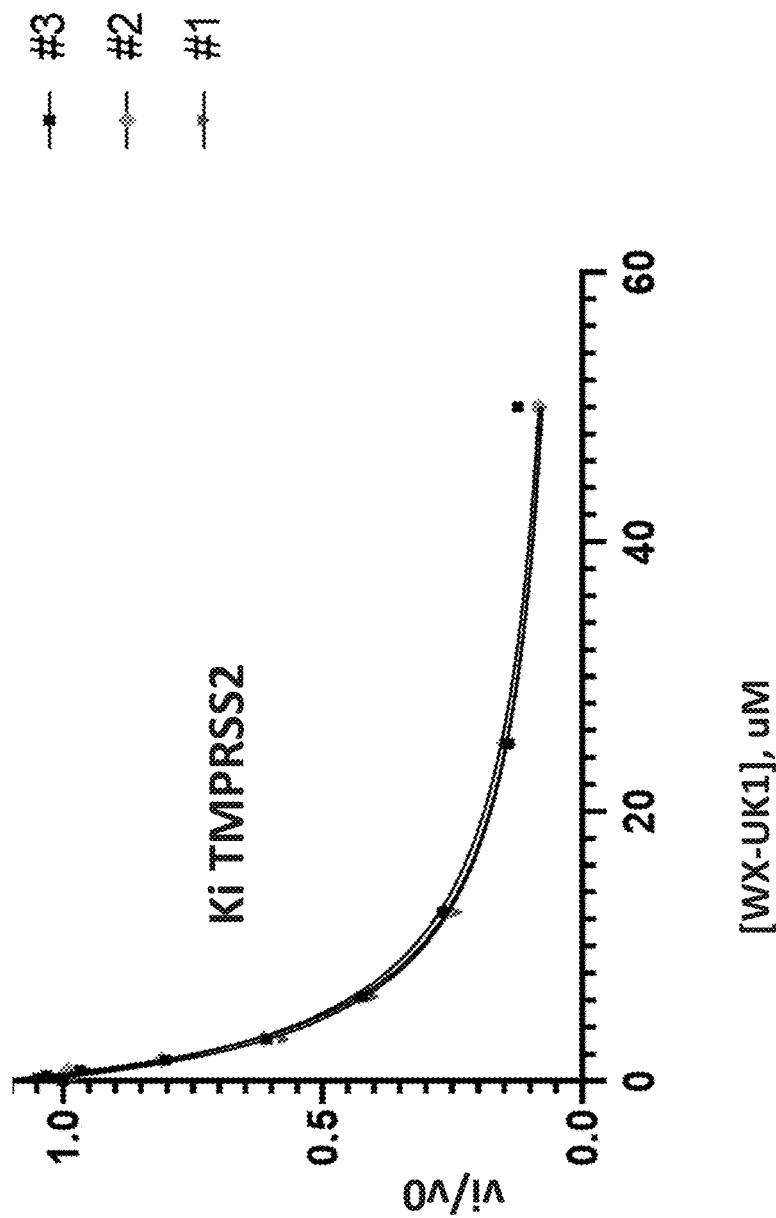
FIG. 1 is a curve fitting equation 1 with the fractional velocity on the y-axis and WX-UK1 concentration on the x-axis. The graph shows how WX-UK1 inhibits the activity of TMPRSS2

As used herein, the term "agent" refers to a drug substance having pharmacological activity—an effect of the agent on an individual. The terms "agent," "active ingredient", "drug substance," and "compound" are used interchangeably herein.

As used herein, the term WX-671 refers to (N-α-(2,4,6-triisopropylphenylsulfonyl)-3-hydroxyamidino-phenylalanine-4-ethoxycarbonylpiperazide) as (L)- or (D)-enantiomers, and as E- or (Z)-isomers or (E/Z)-mixtures, and as free bases or as salts thereof. In the case of compounds, salts, prodrugs or solvates that are solids, it is understood by those skilled in the art that the inventive compounds, salts, and solvates may exist in different crystal forms, all of which are intended to be within the scope of the present invention. WX-671.1 (upamostat) is a specific crystalline salt form of WX-671.

Amounts and weights mentioned in this disclosure typically refer to the free form (free base) (i.e., non-salt, hydrate or solvate form). The typical values described herein represent free-form equivalents, i.e., quantities as if the free form would be administered. If salts are administered the amounts need to be calculated in function of the molecular weight ratio between the salt and the free form. The weight of active compound in the dosage form described herein is with respect to either the free form or the salt form of the compound unless otherwise specifically indicated. For example, about 231 mg of WX-671.1 (upamostat) is the equivalent to approximately 200 mg of WX-671 (the free form).

As used herein, the term "coronavirus" includes naturally occurring (e.g. wild-type) coronavirus; naturally occurring coronavirus variants; and coronavirus variants generated in the laboratory, including variants generated by selection, variants generated by chemical modification, and genetically modified variants (e.g., coronavirus modified in a laboratory by recombinant DNA methods). In an embodiment, a subject can be tested for a viral infection within a few days after symptoms begin, or after treatment according to the present disclosure, by collecting nasal secretions (nasal or nasopharyngeal (NP) swabs), throat (oropharyngeal) swab, blood, or other body fluid samples and testing the sample for detection of viral antigens or RNA in blood and other body fluids using, for example, an antigen-capture enzyme-linked immunosorbent assay (ELISA), using an IgM ELISA (to determine whether the subject has IgM antibodies), using an IgG ELISA (to determine whether the subject has IgG antibodies), using polymerase chain reaction (PCR), or by virus isolation. In an embodiment, the coronavirus is selected from the group consisting of Middle East respiratory syndrome (MERS), severe acute respiratory syndrome (SARS) and SARS-CoV-2.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The terms "co-administer," "coadministration," or "in combination" are used to describe the administration of a compound of the present invention in combination with at least one other antiviral active agent. The timing of the coadministration is best determined by the medical specialist treating the patient. It is sometimes desired that the agents be administered at the same time. Alternatively, the drugs selected for combination therapy may be administered at different times to the patient. Of course, when more than one viral or other infection or other condition is present, the present compounds may be combined with other agents to treat that other infection or condition as required.

As related to the present invention, the term "treatment", "treating", and the like, is defined as prior to prophylactic administration of the compounds in the methods described herein, prior to viral infection, or inhibiting viral activity after infection has occurred. In an embodiment, the term "treating" is meant to administer one or more compounds of the present invention to measurably inhibit the replication of a virus in vitro or in vivo, to measurably decrease the load of a virus in a cell in vitro or in vivo, or to reduce at least one symptom associated with having a CoV-mediated disease in a patient. Desirably, the inhibition in replication or the decrease in viral load is at least 10%, 15%, 20%, 25%, 30%, 35%, 40%, 45%, 50%, 55%, 60%, 65%, 70%, 75%, 80%, 85%, 90%, 95%, 97%, 98%, 99%, as determined using a suitable assay. Assays that monitor replication of viruses include, but are not limited to, cytopathic viral assays, reporter-virus and reporter-cell assays, viral replicon assays, and gene-targeted viral assays. Viral load testing can be carried out using nucleic acid amplification based tests (NATs or NAATs) and non-nucleic acid-based tests on blood plasma samples to determine the quantity of virus in a given volume including viral RNA levels in plasma and tissue and total viral DNA. Alternatively, in certain embodiments, treatment is observed by a trained physician as an appreciable or substantial relief of symptoms in a patient with a CoV-mediated disease. Typically, a decrease in viral replication is accomplished by reducing the rate of RNA polymerization, RNA translation, protein processing or modification, or by reducing the activity of a molecule involved in any step of viral replication (e.g., proteins or coded by the genome of the virus or host important for viral replication). In an embodiment, the term "treat" refers to the ability of a compound or compounds of the present invention to inhibit or suppress replication of a virus, such as an RNA virus. In an embodiment, the term "treat" refers to the ability of a compound or compounds of the present invention to inhibit the cytopathic effect during a RNA virus infection.

In some embodiments, an "effective amount" or "immune-stimulatory amount" of a compound of the invention is an amount which, when administered to a subject, is sufficient to engender a detectable immune response. In other embodiments, a "protective effective amount" of an immunogenic composition is an amount which, when administered to a subject, is sufficient to confer protective immunity upon the subject. In other embodiments, a "therapeutic effect amount" of a compound is an amount which, when administered to a subject, is sufficient to treat a viral infection, such as increase viral clearance.

The agents and methods of the present invention may be utilized to treat a subject in need thereof. In certain embodiments, the subject is a mammal such as a human, or a non-human mammal. When administered to an animal, such as a human, the agent is preferably administered as a pharmaceutical composition comprising, for example, at least one agent of the invention with a substance or collection of substances capable of being combined with the at least one agent. The term "pharmaceutically-acceptable carrier materials" as used herein means a substance or collection of substances capable of being combined with an agent that is suitable for use in contact with the tissues of mammals for purposes of a therapeutic treatment in the mammals under anticipated exposure conditions. Pharmaceutically-acceptable carrier materials are well known in the art and include, for example, inert solid, semi-solid or liquid filler, diluent, encapsulating material. Pharmaceutically-acceptable carrier materials must, of course, be of sufficiently high purity and sufficiently low toxicity to render them suitable for administration to the human or lower animal being treated. The pharmaceutical composition can be in unit dosage form such as tablet, capsule (including sprinkle capsule and gelatin capsule), granule, powder, syrup, suppository, injection or the like.

The term "immune response" refers to a response of a cell of the immune system, such as a B-cell, T-cell, macrophage or polymorphonucleocyte, to a stimulus such as an antigen. An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection).

By "more effective" is meant that a treatment exhibits greater efficacy, or is less toxic, safer, more convenient, or less expensive than another treatment with which it is being compared. Efficacy may be measured by a skilled practitioner using any standard method that is appropriate for a given indication.

As used herein, the term "a suitable period of time" refers to the period of time starting when a patient begins treatment for a diagnosis of coronavirus infection using a method of the present disclosure, throughout the treatment, and up until when the patient stops treatment due to either a reduction in symptoms associated with the coronavirus infection or due to a laboratory diagnosis indicating that the viral infection is under control. In an embodiment, a suitable period of time is one (1) week. In an embodiment, a suitable period of time is between one (1) week and two (2) weeks. In an embodiment, a suitable period of time is two (2) weeks. In an embodiment, a suitable period of time is between two (2) weeks and three (3) weeks. In an embodiment, a suitable period of time is three (3) weeks. In an embodiment, a suitable period of time is between three (3) weeks and four (4) weeks. In an embodiment, a suitable period of time is four (4) weeks. In an embodiment, a suitable period of time is between four (4) weeks and five (5) weeks. In an embodiment, a suitable period of time is five (5) weeks. In an embodiment, a suitable period of time is between five (5) weeks and six (6) weeks. In an embodiment, a suitable period of time is six (6) weeks. In an embodiment, a suitable period of time is between six (6) weeks and seven (7) weeks. In an embodiment, a suitable period of time is seven (7) weeks. In an embodiment, a suitable period of time is between seven (7) weeks and eight (8) weeks. In an embodiment, a suitable period of time is eight (8) weeks.

As used herein, the term "cytopathic effects" refers to the changes in cell morphology due to a viral infection.

As used herein, the terms "cytopathogenesis" or "pathogenesis" includes inhibition of host cell gene expression and includes other cellular changes that contribute to viral pathogenesis in addition to those changes that are visible at the microscopic level.

As used herein, the term "inhibitor" refers to a molecule that affects the activity of enzymes. The inhibitors of the present invention are reversible meaning they form weak interactions with their target enzyme and are easily removed. A reversible inhibitor forms a transient interaction with an enzyme. The strength of the binding between an enzyme and a reversible inhibitor is defined by the dissociation constant ($K_d$). The smaller the value of $K_d$ the stronger the interaction between the enzyme and inhibitor and the greater the inhibitory effect. When talking about enzyme inhibition $K_d$ is referred to as $K_i$.

The term "in vitro" as used herein refers to procedures performed in an artificial environment, such as for example, without limitation, in a test tube or cell culture system. The skilled artisan will understand that, for example, an isolate SK enzyme may be contacted with a modulator in an in vitro environment. Alternatively, an isolated cell may be contacted with a modulator in an in vitro environment.

The term "in vivo" as used herein refers to procedures performed within a living organism such as, without limitation, a human, monkey, mouse, rat, rabbit, bovine, equine, porcine, canine, feline, or primate.

DETAILED DESCRIPTION

The disclosure relates generally to the fields of virology, infectious disease, and medicine. And describes compounds, compositions, methods and kits for the treatment of CoV-mediated disease, e.g., one caused by SARS-CoV-2, SARS, or MERS. In an embodiment, the compositions comprise WX-671 and a pharmaceutically-acceptable carrier material. In an embodiment, the present disclosure describes a new use/application of upamostat in the preparation of medicines for treating coronavirus infection in humans.

More specifically, the invention relates to effective inhibitors of coronaviruses which can treat coronaviruses, including the 2019 novel coronavirus. The invention provides a new use of upamostat as an effective inhibitor of coronaviruses, and its application in the preparation of drugs for treating coronavirus infection in humans.

WX-671, (N-α-(2,4,6-triisopropylphenyl sulfonyl)-3-hydroxyamidino-phenylalanine-4-ethoxycarbonylpiperazide), is an orally active prodrug of the potent serine protease inhibitor WX-UK1 (N-α-(2,4,6-triisopropylphenylsulfonyl)-3-amidino-phenylalanine-4-ethoxycarbonylpiperazide). WX-671 is represented by the following structural formula:

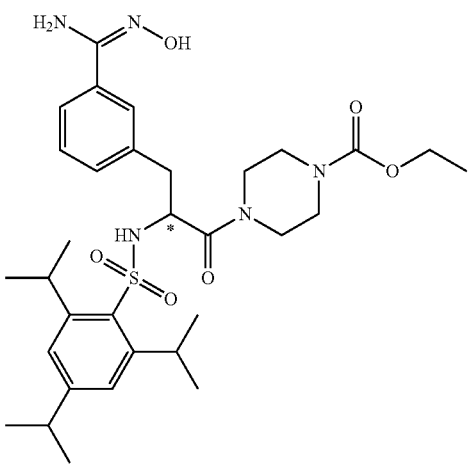 [SMILES: CCOC(=O)N1CCN(C(=O)C(Cc2cccc(/C(N)=N\O)c2)NS(=O)(=O)c2c(C(C)C)cc(C(C)C)cc2C(C)C)CC1]

and can be prepared as (L)- or (D)-enantiomers, and as E- or (Z)-isomers or (E/Z)-mixtures, and as free bases or as salts thereof.

WX-671 is a prodrug. As used herein, a prodrug refers to a pharmaceutical composition that includes a biologically inactive compound that is metabolized in vivo to generate the active form of the drug. WX-671 is a compound which is convertible in vivo to afford WX-UK1. WX-UK1 can only be administered by intravenous infusion. WX-UK1 is used in many of the experimental in vitro examples described herein. While the present disclosure describes the oral WX-671 compound as a medicament, it should be understood that a medicament can be made using the intravenous infusion compound WX-UK1, which is within the scope and spirit of the present invention. U.S. Pat. Nos. 6,861,435, 7,247,724, 7,659,396, and 9,089,532, which are incorporated herein by reference, disclose WX-UK1 and methods of making same.

WX-671.1, N-α-(2,4,6-triisopropylphenylsulfonyl)-3-hydroxyamidino-(L)phenylalanine-4-ethoxycarbonylpiperazide hydrogen sulfate, also referred to as Ethyl 4-{3-[(E)-amino(hydroxyimino)methyl]-N-[(2,4,6-triisopropylphenyl)sulfonyl]-L-phenylalanyl}piperazine-1-carboxylate hydrogen sulfate, has the molecular formula $C_{32}H_{47}N_5O_6S \times H_2SO_4$ and a molecular mass of 727.91 g/mol (free base: 629.83 g/mol). U.S. Pat. Nos. 6,624,169, 7,211,670, 7,247,724, 7,342,018, 7,608,623, 7,659,396, 7,713,980, 7,745,441, 7,807,681, 7,884,206, 7,951,943, 8,492,385, 8,692,761 and RE46424, which are incorporated herein by reference, disclose these compounds, use, and methods of making same. The substance WX-671.1 has been given an international nonproprietary name (INN) of upamostat.

The structural formula of WX-671.1 (upamostat) is as follows:

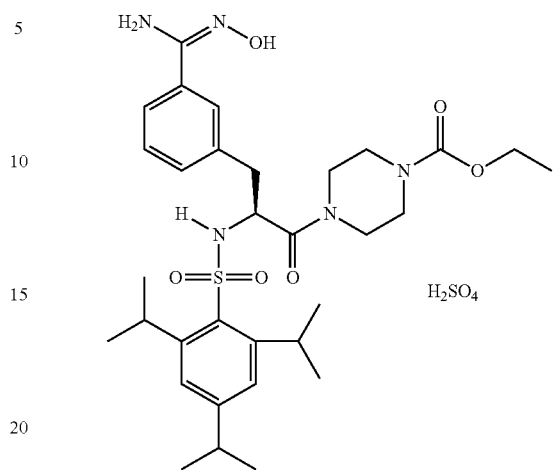

Upamostat is a non-hygroscopic, white to yellowish powder which is freely soluble in dimethyl sulfoxide and soluble in ethanol. The drug substance is very slightly soluble in water or 0.1 M HCl. Solid preparations for oral administration can be prepared as tablets, pills, powder, granules, capsules and so forth. In an embodiment, these solid preparations are manufactured by adding at least one pharmaceutically-acceptable carrier material such as starch, calcium carbonate, sucrose, lactose, or gelatin. In addition, lubricants such as magnesium stearate, and talc may be used in addition to the typical excipients.

In an embodiment, a medicine is prepared by filling upamostat in hard gelatin capsules that further comprise at least one of the following excipients: microcrystalline cellulose; hypromellose; ethyl alcohol anhydrous; purified water and magnesium stearate vegetal. In an embodiment, upamostat capsules contain upamostat hydrogen sulphate 231.26 mg (equivalent to 200 mg free base). After oral administration, upamostat is converted to the active WX-UK1, which inhibits several serine proteases. Because upamostat can be provided as an oral formulation, it can obviate the disadvantages associated with intravenous administration of other drugs that might be useful for treating coronavirus infection.

Upamostat for treating coronavirus infection is generally administered in an amount ranging from about 200 mg to about 1000 mg per day. In an embodiment, upamostat is administered as one capsule, once per day, for a total daily dose of about 231.26 mg (equivalent to 200 mg free base). In an embodiment, upamostat is administered as two capsules, once per day, for a total daily dose of about 462.52 mg (equivalent to 400 mg free base). In an embodiment, a patient with a confirmed coronavirus infection is provided with instructions to take one capsule of upamostat each day (equivalent to 200 mg upamostat free base), for a total of 2 consecutive weeks, or 14 consecutive days. In an embodiment, a patient with a confirmed coronavirus infection is provided with instructions to take two capsules of upamostat each day equivalent to 400 mg upamostat free base), for a total of 2 consecutive weeks, or 14 consecutive days.

The inventors have discovered the new use of upamostat after a lot of research. Without being bound by theory, it is believed that the serine protease inhibitor WX-UK1, the active drug of upamostat once upamostat is broken down inside the body, is active against at least one of the serine proteases that appear to be responsible for viral spike (S) protein priming. Use of protease inhibitors such as WX-UK1 (or it's prodrug WX-671) may therefore be effective in decreasing CoV activation and spread, resulting in an effective preventative and therapeutic treatment. Therefore, WX-UK1 is able to block SARS-2-S-driven entry into cells, and thus, as a result, will inhibit coronavirus replication. In an embodiment, since infection requires proteolytic activation which facilitates interaction of the virus with host cell receptors, thus enhancing infectivity and spread, upamostat of the present invention, when administered at therapeutically effective amounts and for a suitable period of time, will protect against infection by coronavirus.

Provided herein are packaged pharmaceutical products, also known as pharmaceutical kits, that includes a container, a plurality of upamostat dosage forms suitable for oral administration in the container, and a legend (e.g., a label or an insert) associated with the container and indicating administration of upamostat for treating coronavirus infection. In an embodiment, the legend includes instructions for carrying out the methods described above and/or how to use the kit. Instructions included in the kit can be affixed as a label to packaging material or can be included as a package insert. While instructions are typically written or printed materials, they are not limited to such. Any medium capable of storing instructions and communicating them to an end user is contemplated by this disclosure. Such media include, but are not limited to, electronic storage media (e.g., magnetic discs, tapes, cartridges), optical media (e.g., CD ROM), and the like. As used herein, the term "instructions" can include the address of an internet site which provides instructions.

Combination and Alternation Therapy

The compounds described herein can be administered on top of the current standard of care for COVID patients, or in combination or alternation with any other compound or therapy that the healthcare provider deems beneficial for the patient. The combination and/or alternation therapy can be therapeutic, adjunctive, or palliative. When the methods include administering to a patient more than one active agent, the agents may be administered within 7, 6, 5, 4, 3, 2 or 1 days; within 24, 12, 6, 5, 4, 3, 2 or 1 hours, within 60, 50, 40, 30, 20, 10, 5 or 1 minutes; or substantially simultaneously. The methods of the invention may include administering one or more agents to the patient by oral, systemic, parenteral, topical, intravenous, inhalational, or intramuscular administration.

It has been observed that COVID patients can pass through various stages of disease, and that the standard of care can differ based on what stage of illness the patient presents with or advances to. COVID is noteworthy for the development of "cross-talk" between the immune system and the coagulation system. As the disease progresses, the patient can mount an overreaction by the immune system, which can lead to a number of serious implications, including a cytokine storm. Via the cross-talk between the immune system and the coagulation system, the patient can begin clotting in various areas of the body, including the respiratory system, brain, heart and other organs. Multiple clots throughout the body have been observed in COVID patients, requiring anticoagulant therapy. It is considered that these clots may cause long term, or even permanent damage if not treated and disease alleviated.

More specifically, COVID-19 has been described as progressing through three general stages of illness: stage 1 (early infection), stage 2 (pulmonary phase), and stage 3 (hyperinflammation phase/cytokine storm).

Stage 1 is characterized by non-specific, and often mild, symptoms. Viral replication is occurring, and it is appropriate to begin immediate treatment with the compounds described herein and perhaps in combination or alternation with another anti-viral therapy. Interferon-β may also be administered to augment the innate immune response to the virus. In one embodiment, therefore, a compound of the present invention is used in an effective amount in combination or alternation with interferon-β and or an additional anti-viral drug. Zinc supplements and or Vitamin C is also sometimes administered at this stage or as the illness progresses.

Stage 2 of COVID-19 is the pulmonary phase where patients may experience acute hypoxemic respiratory failure. In fact, the primary organ failure of COVID-19 is hypoxemic respiratory failure. It has been shown that moderate immunosuppression via a steroid, for example, dexamethasone, can be beneficial to patients with acute hypoxemic respiratory failure and/or patients on mechanical ventilation. In one embodiment, a compound the present invention is used in an effective amount in combination with a corticosteroid which may be a glucocorticoid. Non-limiting examples are budesonide (Entocort EC), bethamethasone, (Celestone), prednisone (Prednisone Intensol), prednisolone (Orapred, Prelone), triamcinolone (Aristospan Intra-Articular, Aristospan Intralesional, Kenalog), methylprednisolone (Medrol, Depo-Medrol, Solu-Medrol), hydrocortisone, or dexamethasone (Dexamethasone Intensol, DexPak 10 Day, DexPak 13 Day, DexPak 6 Day).

The NS5B inhibitor Remdesivir has provided mixed results when given to COVID19 patients. It can only be administered in a hospital setting, and only by intravenous injection, typically three times a day, which makes it inappropriate for mild to moderate COVID19 patients. In one embodiment, a compound of the present invention is administered in combination or in alternation with Remdesivir to amplify the overall antiviral effect.

Stage 3, the final stage of the disease, is characterized by progressive disseminated intravascular coagulation (DIC), a condition in which small blood clots develop throughout the bloodstream. This stage also can include multi-organ failure (e.g. vasodilatory shock, myocarditis). It has also been observed that many patients respond to this severe stage of COVID-19 infection with a "cytokine storm." There does appear to be a bi-directional, synergistic relationship between DIC and cytokine storm. To combat DIC, patients are often administered an anti-coagulant agent, which may, for example, be an indirect thrombin inhibitor or a direct oral anticoagulant ("DOAC"). Non-limiting examples are low-molecular weight heparin, warfarin, bivalirudin (Angiomax), rivaroxaban (Xarelto), dabigatran (Pradaxa), apixaban (Eliquis), or edoxaban (Lixiana). In one embodiment, a compound of the present invention is administered in combination or in alternation with anti-coagulant therapy. In some severe cases of clotting in COVID patients, TPA can be administered (tissue plasminogen activator).

It has been observed that high levels of the cytokine interleukin-6 (IL-6) are a precursor to respiratory failure and death in COVID-19 patients. To treat this surge of an immune response, which may constitute a cytokine storm, patients can be administered an IL-6-targeting monoclonal antibody, pharmaceutical inhibitor or protein degrader such as a bispecific compound that binds to IL-6 and also to a protein that mediates degradation. Examples of antibodies include tocilizumab, sarilumab, siltuximab, olokizumab and clazakizumab. In one embodiment, a compound of the present invention is administered in combination or in alternation with tocilizumab or sarilumab. Additional non-limiting examples of immunosuppressant drugs used to treat the overreacting immune system include Janus kinase inhibitors (tofacitinib (Xeljanz)); calcineurin inhibitors (cyclosporine (Neoral, Sandimmune, SangCya)), tacrolimus (Astagraf XL, Envarsus XR, Prograf)); mTOR inhibitors (sirolimus (Rapamune), everolimus (Afinitor, Zortress)); and, IMDH inhibitors (azathioprine (Azasan, Imuran), leflunomide (Arava), mycophenolate (CellCept, Myfortic)). Additional antibodies and biologics include abatacept (Orencia), adalimumab (Humira), anakinra (Kineret), certolizumab (Cimzia), etanercept (Enbrel), golimumab (Simponi), infliximab (Remicade), ixekizumab (Taltz), natalizumab (Tysabri), rituximab (Rituxan), secukinumab (Cosentyx), tocilizumab (Actemra), ustekinumab (Stelara), vedolizumab (Entyvio), basiliximab (Simulect), and daclizumab (Zinbryta)).

IL-1 blocks the production of IL-6 and other proinflammatory cytokines. COVID patients are also sometimes treated with anti-IL-1 therapy to reduce a hyperinflammatory response, for example, an intravenous administration of anakinra. Anti-IL-1 therapy generally may be for example, a targeting monoclonal antibody, pharmaceutical inhibitor or protein degrader such as a bispecific compound that binds to IL-1 and also to a protein that mediates degradation.

Patients with COVID often develop viral pneumonia, which can lead to bacterial pneumonia. Patients with severe COVID-19 can also be affected by sepsis or "septic shock". Treatment for bacterial pneumonia secondary to COVID or for sepsis includes the administration of antibiotics, for example a macrolide antibiotic, including azithromycin, clarithromycin, erythromycin, or roxithromycin. Additional antibiotics include amoxicillin, doxycycline, cephalexin, ciprofloxacin, clindamycin, metronidazole, sulfamethoxazole, trimethoprim, amoxicillin, clavulanate, or levofloxacin. In one embodiment, thus a compound of the present invention, is administered in combination or in alternation with an antibiotic, for example, azithromycin. Some of these antibiotics such as azithromycin have independent anti-inflammatory properties. Such drugs may be used both as anti-inflammatory agents for COVID patients and have a treatment effect on secondary bacterial infections.

A unique challenge in treating patients infected with COVID-19 is the relatively long-term need for sedation if patients require mechanical ventilation which might last up to or greater than 5, 10 or even 14 days. For ongoing pain during this treatment, analgesics can be added sequentially, and for ongoing anxiety, sedatives can be added sequentially. Non-limiting examples of analgesics include acetaminophen, ketamine, and PRN opioids (hydromorphone, fentanyl, and morphine). Non-limiting examples of sedatives include melatonin, atypical antipsychotics with sedative-predominant properties (olanzapine, quetiapine), propofol or dexmedetomidine, haloperidol, and phenobarbital. In one embodiment, a compound of the present invention is administered in combination or in alternation with a pain reliever, such as acetaminophen, ketamine, hydromorphone, fentanyl, or morphine. In one embodiment, a compound of the present invention is administered in combination or in alternation with a sedative, such as melatonin, olanzapine, quetiapine, propofol, dexmedetomidine, haloperidol, or phenobarbital.

Investigational drugs for COVID-19 include chloroquine and hydroxychloroquine. In one embodiment, a compound of the present invention is administered in combination or in alternation with chloroquine or hydroxychloroquine.

A protease inhibitor such as lopinavir or ritonavir, previously approved for HIV, may also be administered.

Additional drugs that may be used in the treatment of a COVID patient include, but are not limited to favipiravir, fingolimod (Gilenya), methylprednisolone, bevacizumab (Avastin), Actemra (tocilizumab), umifenovir, losartan and the monoclonal antibody combination of REGN3048 and REGN3051 or ribavirin. Any of these drugs or vaccines can be used in combination or alternation with an active compound provided herein to treat a viral infection susceptible to such.

In one embodiment, a compound of the present invention is used in an effective amount in combination with anti-coronavirus vaccine therapy, including but not limited to mRNA-1273 (Moderna, Inc.), AZD-1222 (AstraZeneca and University of Oxford), BNT162 (Pfizer and BioNTech), CoronaVac (Sinovac), NVX-CoV 2372 (NovoVax), SCB-2019 (Sanofi and GSK), ZyCoV-D (Zydus Cadila), and CoVaxin (Bharat Biotech). In another embodiment, a compound of the present invention is used in an effective amount in combination with passive antibody therapy or convalescent plasma therapy.

In an embodiment, a compound of the present invention is used in an effective amount in combination with a 5-HT receptor antagonists, which can relieve certain symptoms that might be present in a patient infected with coronavirus, such as diarrhea.

SARS-CoV-2 is constantly mutating, which many increase virulence and transmission rates. Drug-resistant variants of viruses may emerge after prolonged treatment with an antiviral agent. Drug resistance may occur by mutation of a gene that encodes for an enzyme used in viral replication. The efficacy of a drug against an RNA virus infection in certain cases can be prolonged, augmented, or restored by administering the compound in combination or alternation with another, and perhaps even two or three other, antiviral compounds that induce a different mutation or act through a different pathway, from that of the principle drug.

The present invention has multiple aspects, illustrated by the following non-limiting examples. The following examples are given for the purpose of illustrating various embodiments of the invention and are not meant to limit the present invention in any fashion.

EXAMPLES

Example 1: Evaluation of TMPRSS2 and TMPRSS11(A) as Targets for WX-UK1 Inhibition Several enzymes, pertaining to different protease families, can be hijacked by CoV S proteins for priming. The pH-dependent cysteine protease cathepsin L, TMPRSS2, TMPRSS11A, as well as the serine protease furin can prime S proteins during viral entry into target cell. We performed an analysis, including structure modelling/prediction, structure analysis and review of relevant literature to determine if any of the TTSPs are a relevant target of inhibition by upamostat.

TMPRSS2 and TMPRS11A mammalian expression systems were purchased from MyBioSource (MBS1193731 and MBS1345824, respectively). Proteins were reconstituted to 1 mg/ml according to the manufacturer, and we ran a gel with the reconstituted proteins. A fresh stock solution of WX-UK1 was made (100 mM WX-UK1 in 100% DMSO). Concentrated stock was diluted to 1 mM in HBS buffer before further dilution in assays.

Enzyme inhibitors may interact with enzymes and/or enzyme-substrate complexes in several different ways to diminish the rate of an enzyme-catalyzed reaction. For each mode of inhibition, one can calculate a dissociation constant, Ki, for the inhibitor that reflects the strength of the interaction between the enzyme and the inhibitor. Ki for an inhibitor is analogous to Km for a substrate; a small Ki value reflects tight binding of an inhibitor to an enzyme, whereas a larger Ki value reflects weaker binding. The precise formula that is used to calculate Ki depends on the mode of inhibition, which can be determined experimentally by comparing the "apparent" values of $V_{max}$ and Km for an enzyme in the presence of an inhibitor to the $V_{max}$ and Km values in the absence of any inhibitor (Equation 2 below).

The chromogenic substrate chosen for these studies was S-2288 substrate. $K_i$-values were determined by measuring the effect of WX-UK1 on human serine protease cleavage of chromogenic substrates. For determination of $K_i$-values, concentration series of WX-UK1 were pre-incubated with the target human serine protease before chromogenic substrate was added to initiate the reaction. The reaction velocities were determined from the slopes using linear regression and these were normalized to that of the non-inhibited reaction. The normalized activities were plotted against WX-UK1 concentrations before the $K_i$-values were obtained by non-linear regression using equation 1.

$$\frac{v_i}{v_0} = \frac{K_i \cdot KM + [S]}{(K_i \cdot [S]) + KM \cdot (K_i + [I])} \quad \text{Equation 1}$$

vi/v0 is the ratio of initial velocity with and without inhibitor, which is described as a function of inhibitor concentration, [I] and substrate concentration, [S].

The $K_M$-parameter was obtained by standard Michaelis-Menten kinetics. Serine protease was added to a suitable concentration series of substrate, high enough to yield an experimental Vmax value. The subsequent reaction velocities were plotted against the substrate concentrations before the KM-value was derived using the Michaelis-Menten equation (2).

$$v = \frac{v_{max} \cdot [S]}{K_M + [S]} \quad \text{Equation 2}$$

All experiments were performed in at least triplicates at 37° C. in FIBS (30 mM Hepes, pH=7.4; 150 mM NaCl; 0.5% BSA). Reactions were monitored at 2 reads/min for at least 45 min at 405 nm. Since WX-UK1 was kept in 100% DMSO, an uninhibited DMSO-control was included in all experiments to exclude unwanted DMSO effects on protease activity.

Inhibition of Human TMPRSS2 with WX-UK1

FIG. 1 is a curve fitting equation 1 with the fractional velocity on the y-axis and WX-UK1 concentration on the x-axis. The graph shows how WX-UK1 inhibits the activity of TMPRSS2. The $K_i$ was determined to be 2.9±0.04 (3) μM.

Inhibition of Human TMPRSS11a with WX-UK1

Figure 2:
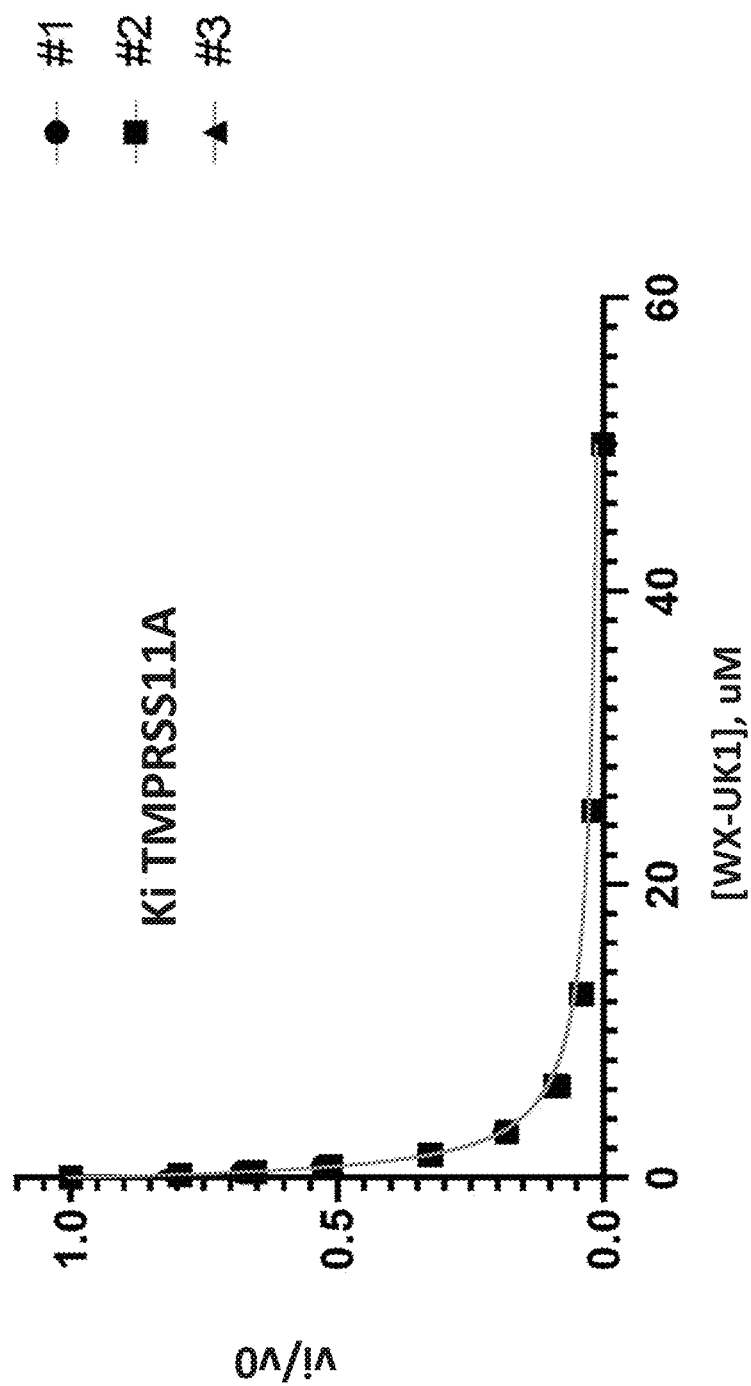
FIG. 2 is a curve fitting equation 1 with the fractional velocity on the y-axis and WX-UK1 concentration on the x-axis. The graph shows how WX-UK1 inhibits the activity of TMPRSS11A.

FIG. 2 is a curve fitting equation 1 with the fractional velocity on the y-axis and WX-UK1 concentration on the x-axis. The graph shows how WX-UK1 inhibits the activity of TMPRSS11A. The $K_i$ was determined to be 0.39±0.01 (3) μM.

TABLE 1 lists inhibition constants, Ki values, of WX-UK1 against a panel of proteases:

| Protease | $K_i$ (μM) Mean ± SD (n) |
|---|---|
| Human Trypsin-3 | 0.019 ± 0.004 (6) |
| Human Trypsin-2 | 0.075 ± 0.003 (6) |
| Human Trypsin-6 | 0.10 ± 0.01 (4) |
| Human Trypsin-1 | 0.19 ± 0.01 (3) |
| Human Matriptase-1 | 0.20 ± 0.01 (3) |
| Human TMPRSS11(A) | 0.39 ± 0.01 (3) |
| Human HATL5 | 0.7 ± 0.1 (3) |
| Human Enterokinase | 0.71 ± 0.04 (4) |
| Human Thrombin | 0.8 ± 0.1 (3) |
| Human uPA | 0.9 ± 0.1 (3) |
| Human FXIa | 0.9 ± 0.1 (3) |
| Human two-chain tPA | 1.4 ± 0.1 (3) |
| Human HAT | 1.5 ± 0.1(6) |
| Human Plasmin | 2.4 ± 0.3 (4) |
| Human FIXa | 2.5 ± 0.2 (3) |
| Human Fxa | 2.6 ± 0.4 (3) |
| Human TMPRSS2 | 2.9 ± 0.04 (3) |
| Human C1s | 3.1 ± 0.4 (5) |
| Human Activated Protein C | 3.9 ± 0.2 (3) |
| Human Hepsin | 4.3 ± 0.5 (5) |
| Human Matriptase-2 | 6.4 ± 0.3 (4) |
| Human Spinesin | 7.7 ± 0.5 (3) |
| Human Tryptase-ε | 11 ± 2 (3) |
| Human DESC-1 | 13 ± 2 (3) |
| Human PRSS27 (IC50) | 19 ± 4 (3) |
| Human Plasma Kallikrein | 26 ± 1 (3) |
| Human HGFA | 28 ± 5 (4) |
| Human Granzyme A | >250 (3) |
| Human Kallikrein-8 | >250 (3) |
| Human Kallikrein-1 | >250 (3) |
| Human Kallikrein-11 | >250 (3) |
| Human Prostasin (IC50) | >250 (3) |
| Rat uPA | 0.4 ± 0.1 (3) |
| Bovine Cationic Trypsin-1 | 0.5 ± 0.1 (6) |
| Canine uPA | 0.7 ± 0.1 (4) |
| Rabbit uPA | 0.8 ± 0.1 (3) |
| Human uPA (Q192A in medium) | 2.9 ± 0.1 (3) |
| Human uPA (H99A in medium) | 14 ± 0.4 (3) |
| Mouse uPA | 45 ± 6 (3) |

Example 2: Assessment of the Anti-Viral Activity of Upamostat and WX-UK1 Against SARS-CoV-2 in Human Airway Epithelial Cells We designed an in vitro assessment in an organotypic air-liquid-interface (ALI) culture of human primary bronchial epithelial cells (HBEC; EpiAirway™, MatTek) to evaluate whether infection and spread of SARS-CoV-2 could be directly inhibited by upamostat and WX-UK1. This human cell culture model system was selected because it contains a pseudostratified epithelial layer that morphologically and functionally resembles that of the human airway, consisting of ciliated and goblet (mucus producing) cells exposed to the air from the apical layer. These cells act as the first line of defense against invading viruses and serve as replication sites. Available evidence also suggests that human bronchial epithelial cells express host factors targeted by upamostat (e.g., TMPRSS2).

Test Compounds:
Upamostat—Test Compound
  Description: Upamostat—ethyl 4-{3-[(E)-amino(hydroxyimino)methyl]-N-[(2,4,6-triisopropylphenyl)sulfonyl]-L-phenylalanyl}-piperazine-1-carboxylate hydrogen sulphate.

Solvent: DMSO
WX-UK1—Test Compound
   Description: WX-UK1—ethyl 4-[(2S)-3-(3-carbamimidoylphenyl)-2-[(2,4,6-triisopropylphenyl)sulfonylamino]propanoyl]piperazine-1-carboxylate.
   Solvent: DMSO
Camostat Mesylate—Test Compound
   Description: Camostat mesylate (CM) 4-[[4-[(Aminoiminomethyl)amino]benzoyl]oxy] benzeneacetic acid 2-(dimethylamino)-2-oxoethyl ester methanesulfonate; FOY 305; FOY-S 980; Foipan mesylate. Camostat is a synthetic, orally bioavailable serine protease.
   Solvent: DMSO
Bleomycin (Sulfate)—Positive Cytotoxic Control
   Description: Bleomycin is a chemotherapy agent commonly used for the treatment of Hodgkin's lymphoma and embryonal carcinomas. A broad spectrum of bleomycin-induced pulmonary toxicities have been well described as a complication of such therapy, the most common variant of which is bleomycin-induced pneumonitis (BIP) (Sleijfer et al., 2001). Bleomycin (BLM) is chosen as the best-studied micronucleus (MN) inducers in human lymphocytes with different mechanisms of genotoxicity.
   Solvent: DMSO 16.67 mg/mL (11.2 mM)
Methods:
Cell Culture—Differentiated Human Bronchial Epithelial Cells (HBEC)

Figure 3:
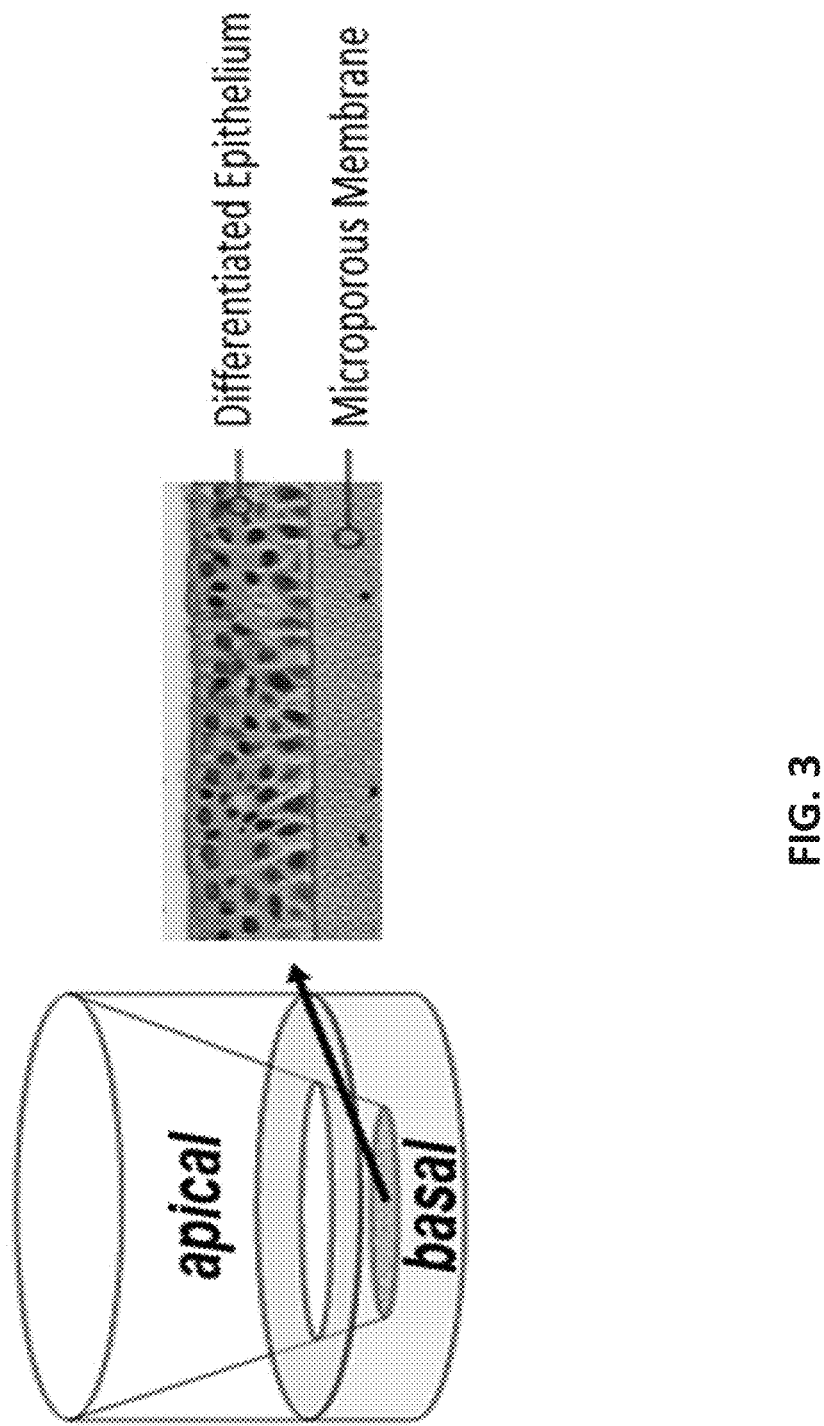
FIG. 3 is a depiction of the human EpiAirway™ cell culture model, herein referred to as human bronchial epithelial cells (HBEC).

Normal human bronchial epithelial (HBEC) cells were differentiated by MatTek Corporation (Ashland, Mass.) and arrived in kits with either 12- or 24-well inserts each. HBEC cells were grown on 6 mm^2 mesh disks in transwell inserts. Three days prior to shipment, the tissues were transferred into hydrocortisone-free medium. During transportation the tissues were stabilized on a sheet of agarose, which was removed upon receipt. One insert was estimated to consist of approximately $1.2 \times 10^6$ cells. Kits of cell inserts (EpiAirway™ AIR-100) originated from a single donor, #9831, a 23-year old, healthy, non-smoking, Caucasian male. The cells have unique properties in forming layers, the apical side of which is exposed only to air and that creates a mucin layer. Upon arrival, the cell transwell inserts were immediately transferred to individual wells of a 6-well plate according to manufacturer's instructions, and 1 mL of MatTek's proprietary culture medium (AIR-100-MM) was added to the basolateral side, whereas the apical side was exposed to a humidified 5% CO2 environment. Cells were cultured at 37° C. for one day before the start of the experiment. After the 16-18 h equilibration period, the mucin layer, secreted from the apical side of the cells, was removed by washing with 400 µL pre-warmed TEER buffer. Culture medium was replenished following the wash step. A depiction of the culture inserts and EpiAirway tissue provided in FIG. 3.

Treatment with Test Compounds:

Test compounds were serially diluted from stock solution (containing DMSO) in Assay medium (AIR-ASY-100, MatTek) and placed at room temperature. Test compound dilutions are outlined below (final DMSO <0.5%). HBEC cultures were washed with phosphate-buffered saline (PBS) and incubated at 37° C. with Bleomycin sulfate (75.6 and 151 µg/ml), upamostat (6 concentrations ranging from 0.12 to 30.00 µg/ml), WX-UK1 (3.33, 10, and 30.00 µg/ml) or camostat (0.5, 5, and 25 µg/ml) diluted in assay medium (AIR-100-ASY, MatTek) for 1 h prior to infection. For control wells, assay medium with DMSO (final DMSO <0.5%; control) and virus only control (assay medium only) were added for the 1 h before infection. Compounds were added to each insert on the apical layer (0.15 mL) and basal layer (0.85 mL) in triplicate.

Viral Infection and Sample Processing:

After 1 hr incubation with compounds, the apical side of the cultures were washed and then infected with SARS-CoV-2 clinical isolate (2019-nCoV/USA-WA1/2020) at MOI=0.1 PFU/cell for 1 h at 37° C., in the presence of compound or assay control media. After 1 hr viral incubation, the virus was removed from the apical side, and cultures were washed one time with PBS to remove any unbound virus. The cultures were then incubated at 37° C. for 72 h with fresh compound. At 24 h and 48 h post-infection, the basolateral medium was replaced with 1 mL of fresh medium containing the respective compounds.

At 72 hours post-infection, tissues and media were collected for processing. The apical layer was washed with 0.4 mL of TEER buffer (PBS with $Mg^{2+}$ and $Ca^{2+}$) and collected for viral titer assessment via TCID50 (50% tissue culture infectious dose) assay. Eight-fold serial dilutions of apical layer supernatant sample concentrations were added to 96-well assay plates containing Vero E6 cells (20,000/well). The plates were incubated at 37° C., 5% CO2 and 95% relative humidity. Following 3 days (72±4 h) incubation, the plates were stained with crystal violet to measure cytopathic effect (CPE). Virus titers were calculated using the method of Reed and Muench (Reed et al., 1938). The TCID50 values were determined from triplicate samples. To confirm results from the TCID50 assay, a plaque reduction assay was performed. Briefly, 10-fold serial dilutions of apical layer supernatant sample concentrations were added to 24-well assay plates containing VeroE6 cell (100,000 cells/well) for plaque reduction assay. The plates were incubated at 37° C., 5% CO2 and 95% relative humidity. Following 3 days (72±4 h) incubation, the plates were fixed with 5% neutral buffered formalin and stained with crystal violet to visualize plaques. The titer was calculated in PFU/mL using the following formula: Titer (PFU/mL)=number of plaques counted$\times 10^{d}$ ilution counted$\times 10$ (to get to mL because we added 100 µL of diluted sample). The assay was performed twice, with a second assay being conducted on virus+DMSO and 0.2 ug/ml upamostat to evaluate additional sample dilutions.

To evaluate the health of HBEC cells after exposure to opaganib, control compounds, and viral infection, a Lactate dehydrogenase (LDH) release assay was conducted. Medium from the basolateral layer of the tissue culture inserts was removed 72 hours post-infection and diluted in LDH Storage Buffer as per the manufacturer's instructions (Promega). Samples were further diluted with LDH Buffer and incubated with an equal volume of LDH Detection Reagent. Luminescence was recorded after 60 minutes incubation at room temperature. A no cell control was included as a negative control to determine culture medium background and bleomycin included as a positive cytotoxic control. Luminescence was reported, with background levels found within the acceptable luminescence range (range 1,000-10,000).

Additionally, the apical layer of the HBEC tissues were collected by adding Trizol LS (Invitrogen) to each culture insert and pipetting up and down several times to lyse and collect the cells and store at −80° C. for future RNA and protein expression analysis.

Results:

Upamostat and WX-UK1, are Highly Potent Antiviral Inhibitors of SARS-CoV-2 in Human Bronchial Epithelial Tissue Cultures.

In this study, normal human bronchial epithelial cells (HBEC) were pretreated in triplicate with 6 different concentrations of upamostat (ranging from 0.12 to 30.0 µg/ml) and 3 different concentrations of WX-UK1 (ranging from 3.33 to 30.0 µg/ml) both on the apical and basolateral side of each culture. Once pretreated, HBEC were exposed to SARS-CoV-2 (2019-nCoV/USA-WA1/2020) and incubated for 3 days with compound. At 3 days post infection, the apical layer was washed and assessed for viral load by TCID50 assay. The basolateral media was collected and assessed for presence of lactate dehydrogenase (LDH), which is released from damaged cells serving as an indicator of cell death/viability. For comparison, 3 concentrations of camostat (ranging from 0.5 to 25.0 µg/ml), an established TMPRSS2 inhibitor was included.

Both upamostat and WX-UK1 demonstrated potent anti-viral activity, with replication being inhibited in a dose-dependent manner without significant compromise to cell viability (except for at the highest dose of each compound). A 3-log and 4-log reduction in viral load was observed by TCID50 at the lowest concentration of upamostat (0.12 µg/ml) and WX-UK1 (3.33 µg/ml), respectively. Both upamostat and WX-UK1 saw similar reduction in viral titer at 3 days post infection. Cell viability, as assessed in the LDH release assay, was reported uncompromised at all but the maximum concentrations evaluated for upamostat and WX-UK1.

Figure 4B:
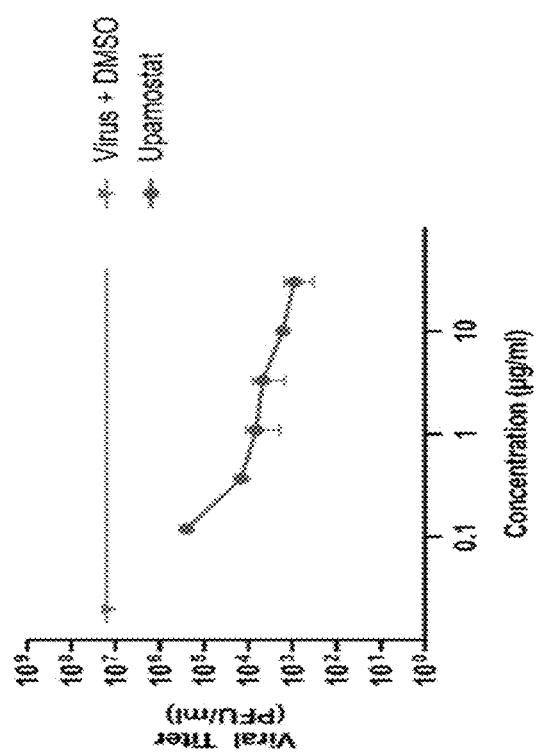
FIG. 4B is a graph showing that in upamostat-treated, SARS-CoV-2 infected HBEC cultures, after 3 days incubation, a dose-dependent reduction in infectious virus production was observed at pharmacologically relevant concentrations. The virus was titered via plaque reduction assay in apical washes. Each symbol represents the titer, averaged from 3 replicates tested.
Figure 4A:
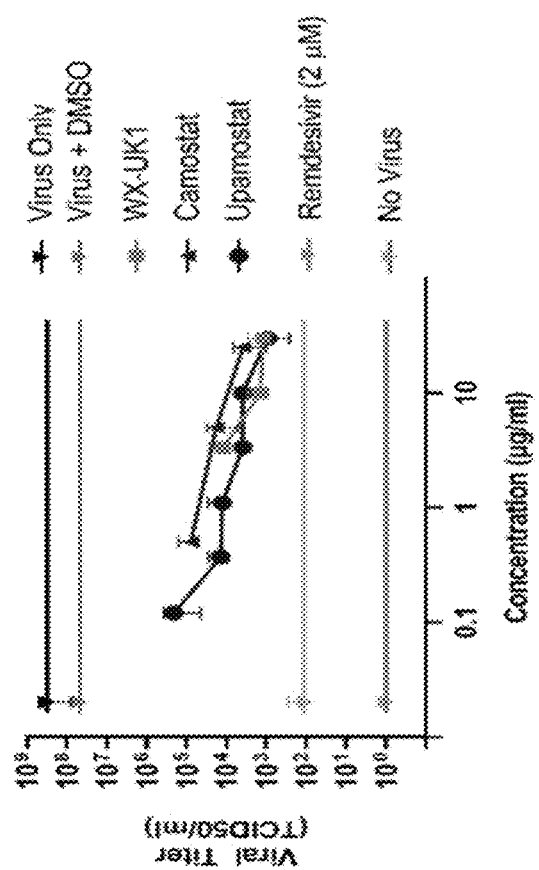
FIG. 4A is a graph showing that in WX-UK1-treated and upamostat-treated, SARS-CoV-2 infected HBEC cultures, after 3 days incubation, a dose-dependent reduction in infectious virus production was observed at pharmacologically relevant concentrations. The virus was titered via TCID50 assay in apical washes. Each symbol represents the titer, averaged from 3 replicates tested.

To demonstrate the anti-viral activity of upamostat and WX-UK1 against SARS-CoV-2 in a human primary epithelial culture system, we performed anti-viral assays in HBEC cultures, which are grown on air-liquid interface and recapitulate the cellular complexity and physiology of the human conducting airway. In upamostat- and WX-UK1-treated, SARS-CoV-2-infected HBEC cultures, after 3 days incubation, a dose-dependent reduction in infectious virus production, confirmed via TCID50 and plaque reduction assay, were observed at pharmacologically relevant concentrations (FIG. 4A and FIG. 4B). These results compare favorably with camostat, a known TMPRSS2 inhibitor.

We calculated an EC50 estimate with the plaque reduction assay result. At the highest concentration tested, inhibition of virus production exceeded 50%. Using graphpad, the EC50 was estimated with the available data. The estimated EC50 was 0.02 ug/ml. We utilized the following formula to calculate % inhibition after converting the TCID values to estimated PFU values as described below:

% inhibition=((Value−Avg virus ctrl)/(Avg Cell Ctrl−Avg virus ctrl)*100)

The % inhibition values were then analyzed via GraphPad following these instructions:
  The X values are upamostat concentrations.
  The Y values are responses.
  Selecting "Dose vs. response curve"
  Selecting Analyze, nonlinear regression, and with the dose-response (stimulation) set of equations and chose [Dose] vs. response—variable slope. All other defaults were accepted. The resulting EC50 was calculated to be 0.02 ug/ml.

Figure 5:
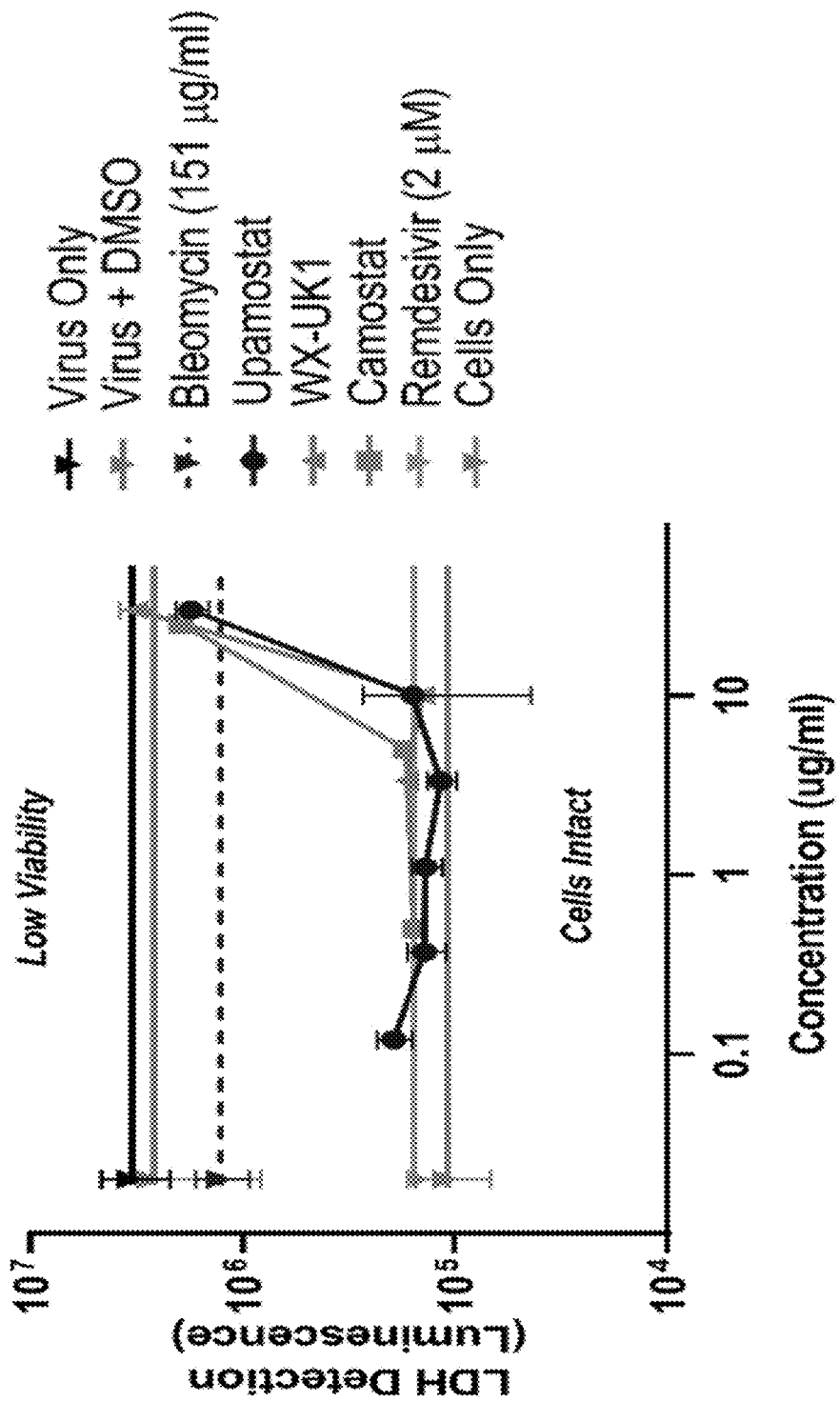
FIG. 5 is a graph showing that in WX-UK1-treated and upamostat-treated, SARS-CoV-2-infected HBEC cultures, after 3 days incubation, limited cytotoxicity across the dose range where the potent anti-viral effects are seen.

Viral replication was inhibited by upamostat, WX-UK1, and camostat without significant compromise to cell viability (except at the highest concentration tested) measured through LDH release. To measure LDH released from non-viable cells, medium from the basolateral layer of the tissue culture inserts was removed 72 hours post-infection and diluted in LDH Storage Buffer as per the manufacturer's instructions (Promega). Samples were further diluted with LDH Buffer and incubated with an equal volume of LDH Detection Reagent. Luminescence was recorded after 60 minutes incubation at room temperature. A no cell control was included as a negative control to determine culture medium background as well as a positive cytotoxicity control, bleomycin (151 ug/ml). Data are plotted using the luminescence values minus the no cell control (average luminescence reading of 6936). This data, using a physiologically relevant human respiratory tissue model, demonstrates upamostat's potential to strongly inhibit SARS-CoV-2 viral replication, with limited cytotoxicity in HBEC cultures across the dose range where the potent anti-viral effects are seen (FIG. 5), further demonstrating upamostat's promising potential for treating patients with COVID-19. The cytotoxic concentration for 50% of the cell culture (CC50) was generated with the available data to determine the compound concentration required to reduce the absorbance of treated cells by 50% in comparison to control cells. The calculated CC50 value for upamostat, using luminescence data generated via the MTT assay, was 46.37 uM (or 29.2 ug/ml). At this CC50 concentration, an EC50 concentration lower than 4.6 uM (or 2.9 ug/ml) would result in an SI value (CC50/EC50) >10.

Example 3: Assessment of the Effects of Upamostat and WX-UK1 on SARS-CoV-2 Spike Protein-Mediated Entry A study was performed to evaluate the inhibitory effects of both upamostat and WX-UK1 against cellular entry of replication defective, single cycle vesicular stomatitis virus (VSV) particles pseudotyped with the SARS-CoV-2 spike protein (VSVpp+SARS-2-S Δ18) or the glycoprotein of vesicular stomatitis virus (VSV) as control. Δ18 refers to the deletion of the 18 C-terminal amino acids of the S protein, which increases pseudotyping efficiency without affecting ACE2 or TMPRSS2 usage. Pseudotype entry and its inhibition was evaluated in Calu-3 and Vero-E6 cells. Calu-3 cells, which are a lung-derived human cancer cell line, allow for SARS-CoV-2 S-driven entry in a TMPRSS2-dependent manner. Agents that inhibit TMPRSS2, including camostat, a known TMPRSS2 inhibitor shown to inhibit SARS-CoV-2 infection of cultured lung cells (Hoffmann et al., 2020), are expected to inhibit S-driven entry in this model. Vero cells, which are a green monkey kidney cell line, permit SARS-CoV-2 spike-driven entry in a TMPRSS2-independent, cathepsin L-dependent manner. Agents that elevate the pH of acidic intracellular endosomes, including chloroquine, are expected to inhibit entry in this model. Entry driven by the G-protein of vesicular stomatitis virus (VSV) served as specificity control (VSV-G driven entry depends on low pH and is thus chloroquine but not camostat sensitive).

Methods:

For pseudotyping, vesicular stomatitis virus pseudotype (VSVpp) were generated according to a published protocol (Berger Rentsch and Zimmer, 2011). In brief, 293T transfected to express the viral surface glycoprotein under study were inoculated with a replication-deficient VSV vector that contains expression cassettes for eGFP (enhanced green fluorescent protein) and firefly luciferase instead of the VSV-G open readingframe, VSV*DG-fLuc (kindly provided by Gert Zimmer, Institute of Virology and Immunology, Mittelhaüsern/Switzerland). After an incubation period of 1 h at 37 C, the inoculum was removed and cells were washed with PBS before medium supplemented with anti-VSV-G antibody (Il, mouse hybridoma supernatant from CRL-2700; ATCC) was added in order to neutralize residual input virus (no antibody was added to cells expressing VSV-G). Pseudotyped particles were harvested 16 h post-inoculation, clarified from cellular debris by centrifugation and used for experimentation.

For transduction, target cells were grown in 96-well plates until they reached 50%-75% confluency before they were inoculated with respective pseudotyped. For experiments involving protease inhibitors, target cells were treated with the respective chemical 2 h before transduction. Transduction efficiency was quantified 16 h posttransduction by measuring the activity of firefly luciferase in cell lysates using a commercial substrate (Beetle-Juice, PJK) and a Hidex Sense plateluminometer (Hidex). The transduction assay measures entry of a single cycle vesicular stomatitis virus (VSV) bearing SARS-CoV-2 spike.

Results:

The ability of upamostat and WX-UK1 to inhibit entry of SARS-2-S and VSV-G bearing pseudotypes was evaluated in Calu-3 (human lung cancer cells) and Vero-E6 cells. Calu-3 cells, which are a lung-derived human cancer cell line, allow for SARS-CoV-2 spike-driven entry in a TMPRSS2-dependent manner and thus a camostat-sensitive fashion. Vero cells, which are an African green monkey derived kidney cell line, permit SARS-CoV-2 spike-driven entry in a cathepsin L-dependent manner and chloroquine-sensitive fashion. Entry driven by the G-protein of vesicular stomatitis virus (VSV) served as specificity control (VSV-G driven entry depends on low pH and is thus chloroquine but not camostat sensitive).

Upamostat and WX-UK1 Inhibit SARS-CoV-2 S Protein Mediated Entry in Human Lung Cancer Cells (Calu-3) and Green Monkey Kidney Cells (Vero E6) with Moderate Efficiency.

Figure 6B:
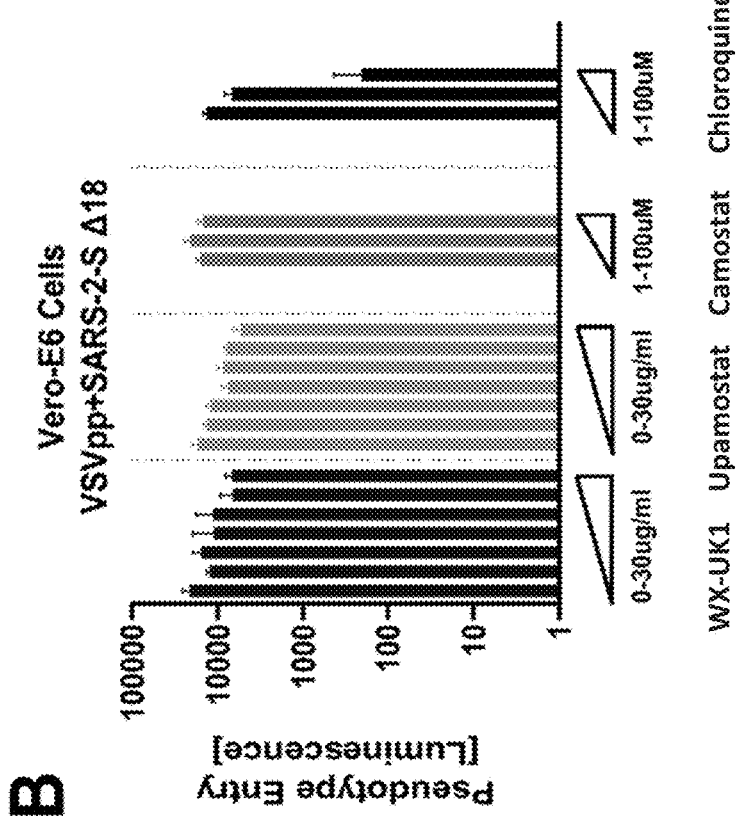
FIG. 6A and FIG. 6B are graphs demonstrating the inhibition by upamostat and WX-UK1 of SARS-2-S-driven entry in Calu-3 cells and Vero-E6 Cells.
Figure 6A:
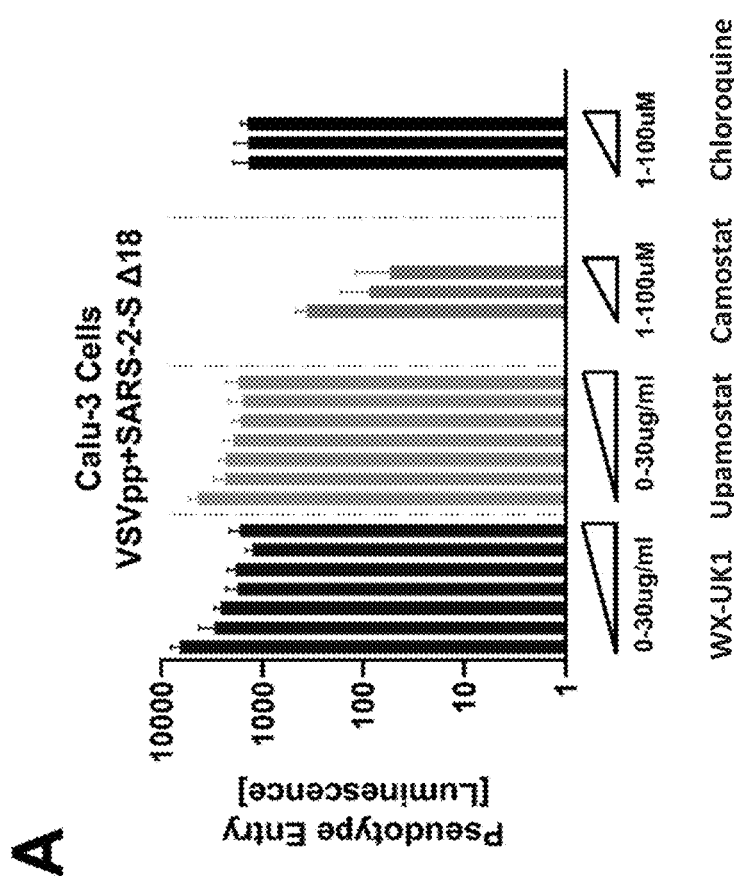
Figure 7:
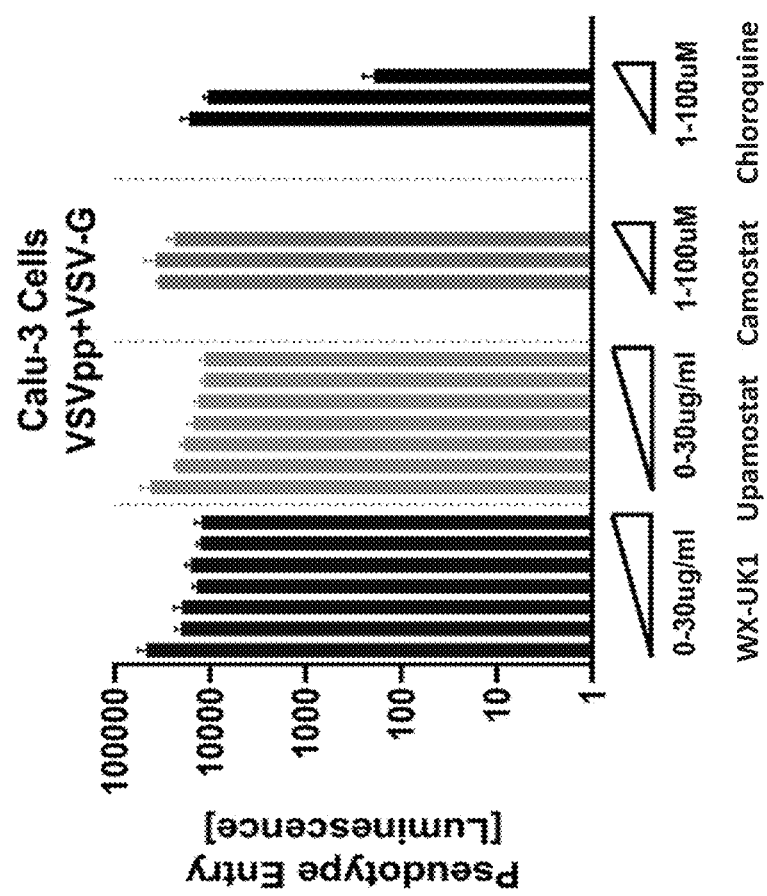
FIG. 7 is a graph demonstrating the inhibition by upamostat and WX-UK1 of VSV-g driven entry in Calu-3 cells. Calu-3 cells were pre-incubated with the indicated concentrations of upamostat, WX-UK1, camostat mesylate, or chloroquine and subsequently inoculated with pseudoparticles harboring the VSV-g protein. Pseudotype entry was analyzed by determining luciferase activity in cell lysates. The results of a single experiment performed with quadruplicate samples are shown. Error bars indicate standard deviation (SD).

When tested against VSVpp+SARS-2-S Δ18 in Calu-3 cells, both WX-UK1 and upamostat showed moderate inhibitory activity, though less than camostat, another serine protease inhibitor (FIG. 6A). When tested in Vero-E6 cells, which do not have surface TMPRSS2, moderate inhibitory activity was still noted for upamostat and WX-UK1; camostat was inactive in this situation while the highest concentration of chloroquine potently inhibited S protein-driven entry (FIG. 6B). WX-UK1 and upamostat moderately inhibited VSV-G entry in Calu-3 cells, suggesting a broader spectrum of activity for upamostat (FIG. 7). All three compounds, except chloroquine, were inactive when tested against VSV-G in Vero76 cells. Overall, these results demonstrate WX-UK1 and upamostat inhibit SARS-CoV-2 spike driven entry into Calu-3 and Vero cells with moderate efficiency. Due to the nature of the model, specific extrapolation to actual in vitro or in vivo inhibitory concentrations is not possible.

Example 4: Randomized, Double-Blind, Placebo-Controlled Phase 2/3 Study of Upamostat, a Serine Protease Inhibitor, or Placebo for Treatment of COVID-19 Disease This study will assess the activity of upamostat against placebo for treatment of COVID-19 patients who, in the investigator's judgment, do not require hospitalization.

Primary Objectives:

Part A of the study: determination of the safety and tolerability of two dose levels and decision regarding upamostat dose for part B. Changes in severity of disease markers will be assessed, but will not be a primary factor in deciding which dose to pursue. Time to recovery will also be calculated, although given the small sample size and expected variability of outcome, a clinically meaningful difference may not be seen.

Part B of the study: comparison between upamostat and placebo in time to sustained recovery from illness. A patient will be considered to have recovered once he or she meets the following criteria:
1) is afebrile (<38.0° C. core temperature) for at least 48 hours without use of antipyretics;
2) all symptoms have resolved or returned to pre-illness levels (e.g., if patient had baseline respiratory compromise prior to the onset of COVID-19), except for:
   a. fatigue, anosmia, ageusia or dysgeusia, which may be persistent at level similar to that during the acute illness, i.e., the same level per symptom questionnaire;
   b. chest pain, cough or dyspnea which if persistent must be at least one grade lower than at the start of treatment and no worse than grade 1 (mild).
   Sustained recovery is recovery, per above definition, maintained for at least 28 days or through end of study, whichever comes first.

Secondary Objectives:

Comparison between active treatment group and placebo of:
1) Proportion of patients who are PCR-negative at days 8, 15, 29 and 57 from the start of treatment (landmark analyses);
2) Time to resolution of individual disease-related symptoms present at baseline;
3) Development of new disease-related symptoms on study;
4) Incidence of pneumonia during study among patients without baseline pneumonia (diagnosed clinically);
5) Changes in laboratory markers of disease severity, i.e., oxygen saturation, CRP, lymphocyte count, cardiac troponin and D-dimer levels, from baseline to time points at which these are measured on study;
6) Adverse events;
7) Hospitalization within 8 weeks after the first dose of study medication, overall and for COVID-19-related indications;
8) Mortality 30 days after first dose of study medication;

Exploratory
1) Percent of patients who report household contacts who have developed symptomatic, PCR-confirmed, COVID-19 by day 57;
2) Levels of serum IgM and IgG antibodies to SARS-CoV-2 at 57 days from the start of treatment.

Safety:

Patients will be followed for adverse events, including both clinical and laboratory events, throughout the course of the study.

In particular, toxicities resulting in dose reductions or discontinuation of therapy will be followed and tabulated.

Population:

Inclusion Criteria:
1. Patients with symptomatic, diagnostically confirmed COVID-19, per RT-PCR assay of respiratory tract sample.
2. Patient must have either become symptomatic or found positive by RT-PCR within 3 days, whichever is greater, of randomization.
3. Males and females ≥age 18 years.

4. At baseline the laboratory parameters listed below are not worse than NCI CTCAE v5.0 grade 2, with exceptions noted below:
    Bilirubin ≤1.5 times upper limit of normal (ULN; grade 1 only)
    AST (SGOT), ALT (SGPT)≤5.0×ULN,
    Serum creatinine ≤1.5×ULN (grade 1)
    Albumin ≥2.0 g/dL
5. Acceptable hematologic status:
    Absolute neutrophil count ≥1000 cells/mm$^3$
    Platelet count ≥50,000 plt/mm$^3$
    Hemoglobin ≥8.0 g/dL
6. Clinically acceptable blood sugar control in the opinion of the investigator.
7. INR and partial thromboplastin time (PTT) each ≤1.5× ULN (i.e., grade 1), unless patient is taking dabigatran or heparin.
8. Oxygen saturation by pulse oximeter ≥92% on room air
9. Negative pregnancy test (if woman of childbearing potential).
10. Females of childbearing potential and males with female partners of childbearing potential must agree to use acceptable contraceptive methods during the study and for at least two months after the last dose of study medication.
11. Ability to complete the daily diary independently.
12. The patient must give informed consent.

Exclusion Criteria:
1. Patient is in need of acute hospitalization per clinician assessment.
2. Pregnant or nursing women.
3. Unwillingness or inability to comply with procedures required in this protocol.
4. Patient requires supplemental oxygen
5. Patient is currently receiving, has received within the past 7 days or is expected to receive during the course of the study remdesivir, chloroquine, hydroxychloroquine, azithromycin or other specific antiviral therapy for COVID-19 or systemic corticosteroid equivalent to ≥0.20 mg daily prednisone/3 mg dexamethasone daily.
6. Patient is currently receiving or has received within 30 days prior to screening any other investigational agent for any indication, including approved agents given for investigational indications (e.g., anti-cytokine treatments).
7. Patient is currently taking or is expected to start taking warafin, apixabain (Eliquis), or rivaroxaban (Xarelto). Patients may be taking or start on study dabigatran (Pradaxa), standard or low molecular weight heparin.

Design:
This is a randomized, double-blind, placebo-controlled, parallel group study of upamostat compared to placebo in patients with symptomatic COVID-19 who do not require inpatient care. The study will use phase 2/3 operationally seamless design methodology for dose selection (part A) and inferentially independent confirmatory phase 3 study (part B). The phase 3 portion will include interim analysis for early termination for futility or increase in sample size, as indicated by initial results.

Methodology:
Part A: After qualification for study, patients will be stratified by age, <65 or ≥65. They will then be randomized 1:1:1 one of the following treatment groups:
1. Upamostat 200 mg two capsules qd (n=20);
2. Upamostat 200 mg one capsule and matching placebo one capsule qd (n=20)
3. Placebo two capsules qd (n=20).

In order to maintain blinding, patients will be given two bottles of medication and instructed to take one pill from each bottle each day. Both pills are to be taken at the same time.

Medication should be taken with water and with or without food.

Patients are to take medication for 14 days or until one of the following occurs:
  Adverse events, whether related or unrelated to study medication which, in the judgement of the investigator, necessitate discontinuation of treatment;
  The patient or investigator decides that it is in the patient's best interest to stop treatment.

An interim analysis will be performed by a data safety monitoring board (DSMB) after a total of 60 patients complete part A.
  If the DSMB determines that safety of both regimens is similar, accrual in part B will continue on the 400 mg qd dose.
  If safety is more favorable with the 200 mg qd regimen, accrual in part B will continue on the 200 mg qd dose.

Part B: Based on safety results from part A, either a 200 mg or 400 mg (i.e., one or two 200 mg capsules) treatment regimen will be selected. Patients enrolled in part B will be stratified by number of the following situations (none, one, or more than one): age ≥65, presence of the following concerning medical conditions: hypertension, chronic lung disease, obesity [BMI≥30], diabetes, heart failure, coronary artery disease, thrombotic events (current or by history), renal disease. Patients will also be stratified by region in which they are treated (US vs non-US). They will then be randomized 3:2 to active drug or placebo at the schedule selected based on part A. A total of approximately 250 additional patients will be enrolled in part B of the study, 150 receiving active drug and 100 receiving placebo. Thus, combining both parts of the study, a total of 170 patients will receive active at the dose selected in part A and 120 will receive placebo. However, analyses will be performed independently for parts A and B.

Patients will complete daily questionnaires about symptoms, including adverse events, vital signs, including temperature and pulse oximetry, and a log of medications taken, daily for the first 4 weeks of study and thrice weekly thereafter. Viral swabs and bloods for safety laboratory and pharmacodynamic markers will be obtained at home visits by medical personnel. After completion of treatment, patients will be followed through day 57 from randomization.

Statistics:
In part A of this study, two dose levels of active drug and placebo will be tested. Based on the incidence and severity of toxicities in each active group, overall assessment of safety by the DSMB, a regimen for part B of the study will be selected. In the absence of marked differences in toxicity between the two active groups, the default choice for continuation into part B will be the 400 mg daily regimen.

Efficacy data from parts A and B will be analyzed separately.

The overall sample size may be expanded based on interim study results.

The sample size was determined based on the primary endpoint, time to sustained recovery from COVID-19 illness, as defined in the primary objective. It was calculated that in order to detect an hazard ratio=1.5 comparing an active group to placebo group with 3:2 allocation ratio a total of 201 recovery events are required, to provide 80% power using a log-rank test at a two-sided significance level of 0.05. Assuming 80% sustained recovery rate by end of follow-up (assumed equal follow-up for all enrolled patients), the minimum number of patients enrolled in part B will be 250 in total, 150 in the active arm on the regimen taken into part B of the study and 100 in the placebo arm.

INDUSTRIAL APPLICABILITY

The present invention provides an anti-coronavirus agent comprising as an active ingredient a compound represented by:

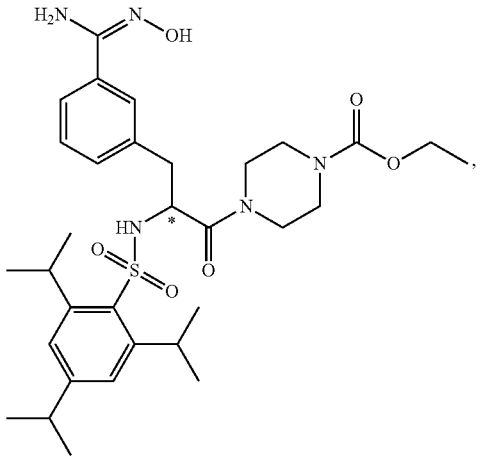 [SMILES: CCOC(=O)N1CCN(C(=O)C(Cc2cccc(/C(N)=N\O)c2)NS(=O)(=O)c2c(C(C)C)cc(C(C)C)cc2C(C)C)CC1]

as (L)- or (D)-enantiomers, and as E- or (Z)-isomers or (E/Z)-mixtures, and as free bases or as salts thereof, an anti-SARS agent comprising the anti-coronavirus agent and a method of treating SARS using the anti-coronavirus agent. The present invention enables the treatment of diseases caused by coronaviruses, especially the SARS-associated coronavirus.

All patents, patent applications, and published references cited herein are hereby incorporated by reference in their entirety. Various modifications and variations of the described compositions and methods of the invention will be apparent to those skilled in the art without departing from the scope and spirit of the invention. Although the invention has been described in connection with specific embodiments, it will be understood that the invention should not be unduly limited to such specific embodiments. Indeed, various modifications of the described modes for carrying out the invention that are obvious to those skilled in the fields of molecular biology, medicine, immunology, pharmacology, virology, or related fields are intended to be within the scope of the invention.

What is claimed is:

1. A method for the treatment of the 2019 coronavirus disease (COVID-19) caused by the SARS-CoV-2 virus comprising administering to a person in need thereof an effective amount of WX-671,

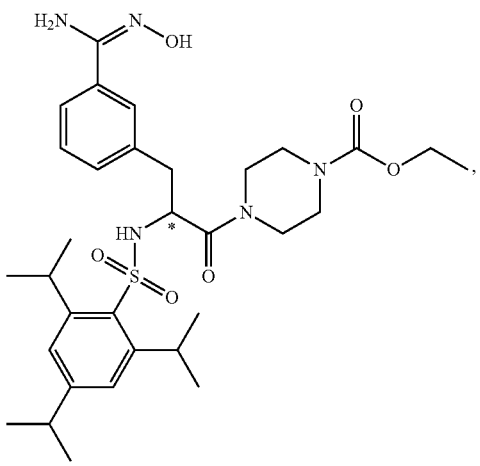 [SMILES: CCOC(=O)N1CCN(C(=O)C(Cc2cccc(/C(N)=N\O)c2)NS(=O)(=O)c2c(C(C)C)cc(C(C)C)cc2C(C)C)CC1]

as (L)- or (D)-enantiomers, and as E- or (Z)-isomers or (E/Z)-mixtures, and as free bases or as salts thereof.

2. The method of claim 1, wherein the WX-671 is in the form of its hydrogen sulfate salt.

3. The method of claim 1, further comprising a pharmaceutically-acceptable carrier material, wherein the WX-671 and the pharmaceutically-acceptable carrier material are in a unit dosage form suitable for oral administration.

4. The method of claim 2, further comprising a pharmaceutically-acceptable carrier material, wherein the WX-671 hydrogen sulfate and the pharmaceutically-acceptable carrier material are in a unit dosage form suitable for oral administration.

5. The method of claim 3, wherein the unit dosage form is a solid dosage form.

6. The method of claim 4, wherein the unit dosage form is a solid dosage form.

7. The method of claim 5, wherein the solid dosage form is a capsule.

8. The method of claim 6, wherein the solid dosage form is a capsule.

9. The method of claim 1, wherein the SARS-CoV-2 virus is wild-type.

10. The method of claim 1, wherein the SARS-CoV-2 virus is a naturally occurring coronavirus variant.

11. The method of claim 2, wherein the SARS-CoV-2 virus is wild-type.

12. The method of claim 2, wherein the SARS-CoV-2 virus is a naturally occurring coronavirus variant.

13. The method of claim 3, wherein the unit dosage form suitable for oral administration is a capsule having 200 mg of WX-671 free base, and wherein administering includes a single capsule administered once each day, for at least 10 days, for a total daily dose of 200 mg of WX-671.

14. The method of claim 3, wherein the unit dosage form suitable for oral administration is a capsule having 200 mg of WX-671 free base, and wherein administering includes two capsules administered once each day, for at least 10 days, for a total daily dose of 400 mg of WX-671.

15. The method of claim 4, wherein the unit dosage form suitable for oral administration is a capsule having about 231 mg of WX-671 hydrogen sulfate, and wherein administering includes a single capsule administered once each day, for at least 10 days, for a total daily dose of about 231 mg of WX-671 hydrogen sulfate.

16. The method of claim 4, wherein the unit dosage form suitable for oral administration is a capsule having about 231 mg of WX-671 hydrogen sulfate, and wherein administering includes two capsules administered once each day, for at least 10 days, for a total daily dose of about 463 mg of WX-671 hydrogen sulfate.

17. A method of treatment comprising administering an effective amount of WX-671,

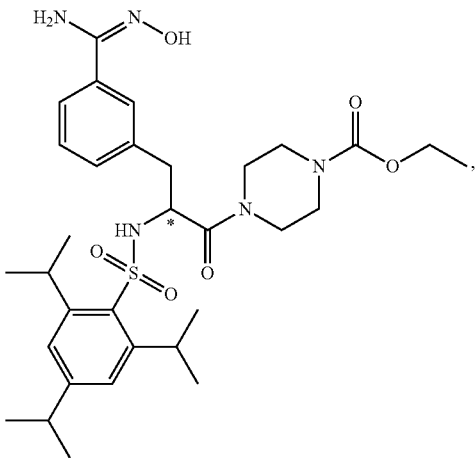 [SMILES: CCOC(=O)N1CCN(C(=O)C(Cc2cccc(/C(N)=N\O)c2)NS(=O)(=O)c2c(C(C)C)cc(C(C)C)cc2C(C)C)CC1]

as (L)- or (D)-enantiomers, and as E- or (Z)-isomers or (E/Z)-mixtures, and as free bases or as salts thereof, to treat a human having 2019 coronavirus disease (COVID-19) caused by the SARS-CoV-2 virus.

18. The method of claim 17, wherein the WX-671 is in the form of its hydrogen sulfate salt.

19. The method of claim 17, further comprising a pharmaceutically-acceptable carrier material, wherein the WX-671 and the pharmaceutically-acceptable carrier material are in a unit dosage unit form suitable for oral administration.

20. The method of claim 18, further comprising a pharmaceutically-acceptable carrier material, wherein the WX-671 hydrogen sulfate and the pharmaceutically-acceptable carrier material are in a unit dosage form suitable for oral administration.

21. The method of claim 19, wherein the unit dosage form is a solid dosage form.

22. The method of claim 20, wherein the unit dosage form is a solid dosage form.

23. The method of claim 21, wherein the solid dosage form is a capsule.

24. The method of claim 22, wherein the solid dosage form is a capsule.

25. The method of claim 17, wherein the SARS-CoV-2 virus is wild-type.

26. The method of claim 18, wherein the SARS-CoV-2 virus is wild-type.

27. The method of claim 17, wherein the SARS-CoV-2 virus is a naturally occurring coronavirus variant.

28. The method of claim 18, wherein the SARS-CoV-2 virus is a naturally occurring coronavirus variant.

29. The method of claim 20, wherein the unit dosage form suitable for oral administration is a capsule having an equivalent of 200 mg of WX-671, and wherein administering includes a single capsule administered once each day, for at least 10 days, for a total daily dose of about 400 mg of WX-671.

30. The method of claim 20, wherein the unit dosage form suitable for oral administration is a capsule having an equivalent of 200 mg of WX-671, and wherein administering includes two capsules administered once each day, for at least 10 days, for a total daily dose of about 400 mg of WX-671.

* * * * *